United States Patent
Sela et al.

(10) Patent No.: US 10,799,316 B2
(45) Date of Patent: Oct. 13, 2020

(54) SYSTEM AND METHOD FOR DYNAMIC VALIDATION, CORRECTION OF REGISTRATION FOR SURGICAL NAVIGATION

(71) Applicant: SYNAPTIVE MEDICAL (BARBADOS) INC., Bridgetown (BB)

(72) Inventors: Gal Sela, Toronto (CA); Cameron Piron, Toronto (CA); Michael Wood, Toronto (CA); Joshua Richmond, Toronto (CA); Murugathas Yuwaraj, Markham (CA); Stephen McFadyen, Toronto (CA); Monroe M. Thomas, Toronto (CA); Wes Hodges, London (CA); Simon Alexander, Toronto (CA); David Gallop, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 77 days.

(21) Appl. No.: 14/775,759

(22) PCT Filed: Mar. 14, 2014

(86) PCT No.: PCT/CA2014/050266
§ 371 (c)(1),
(2) Date: Sep. 14, 2015

(87) PCT Pub. No.: WO2014/139019
PCT Pub. Date: Sep. 18, 2014

(65) Prior Publication Data
US 2016/0000515 A1   Jan. 7, 2016

Related U.S. Application Data

(60) Provisional application No. 61/799,735, filed on Mar. 15, 2013, provisional application No. 61/801,530, (Continued)

(51) Int. Cl.
*A61B 90/00* (2016.01)
*A61B 34/20* (2016.01)
(Continued)

(52) U.S. Cl.
CPC .............. *A61B 90/39* (2016.02); *A61B 34/10* (2016.02); *A61B 34/20* (2016.02); *G06T 7/248* (2017.01);
(Continued)

(58) Field of Classification Search
CPC .................................................. G06T 7/0028
See application file for complete search history.

(56) References Cited

U.S. PATENT DOCUMENTS 5,792,147 A    8/1998   Evans et al.
6,135,946 A    10/2000  Konen et al.
(Continued)

FOREIGN PATENT DOCUMENTS

CN     103083089      5/2013
EP     1708139 A2    10/2006
(Continued)

OTHER PUBLICATIONS

Liao, Hognen, et al. "Real-time 3D-image-guided navigation system based on integral videography." International Symposium on Biomedical Optics. International Society for Optics and Photonics, 2002.
(Continued)

*Primary Examiner* — Serkan Akar
(74) *Attorney, Agent, or Firm* — Thanh V. Vuong

(57) ABSTRACT

Disclosed herein is a system and method for dynamic validation, correction of registration for surgical navigation during medical procedures on a patient which involves confirmation of registration between one or more previously registered virtual objects, such as surgical tools etc. in a
(Continued)

common coordinate frame of a surgical navigation system and an operating room, and intra-operatively acquired imaging during the medical procedure in the common coordinate frame. The method includes displaying intra-operatively acquired imaging of the surgical field containing the one or more real objects corresponding to the one or more previously registered virtual objects, with the real objects being tracked by a tracking system. The method overlaying a virtual image containing the previously registered virtual objects onto the intra-operatively acquired imaging, from the point of view of the intra-operatively acquired imaging, and detecting for any misalignment between any one of the one or more previously registered virtual objects contained in the virtual image and its corresponding real object contained in the intra-operatively acquired imaging.

16 Claims, 22 Drawing Sheets

Related U.S. Application Data filed on Mar. 15, 2013, provisional application No. 61/800,155, filed on Mar. 15, 2013, provisional application No. 61/818,280, filed on May 1, 2013, provisional application No. 61/924,993, filed on Jan. 8, 2014.

(51) Int. Cl.
    *A61B 34/10* (2016.01)
    *G06T 7/246* (2017.01)
    *G06T 7/33* (2017.01)
    *G06T 7/73* (2017.01)
    *A61B 90/50* (2016.01)

(52) U.S. Cl.
    CPC .............. *G06T 7/33* (2017.01); *G06T 7/337* (2017.01); *G06T 7/74* (2017.01); *A61B 90/50* (2016.02); *A61B 2034/104* (2016.02); *A61B 2034/107* (2016.02); *A61B 2034/2048* (2016.02); *A61B 2034/2051* (2016.02); *A61B 2034/2055* (2016.02); *A61B 2090/364* (2016.02); *A61B 2090/373* (2016.02); *A61B 2090/3929* (2016.02); *A61B 2090/3937* (2016.02); *A61B 2090/3983* (2016.02); *G06T 2207/10021* (2013.01); *G06T 2207/10048* (2013.01); *G06T 2207/10076* (2013.01); *G06T 2207/10081* (2013.01); *G06T 2207/10088* (2013.01); *G06T 2207/10104* (2013.01); *G06T 2207/10136* (2013.01); *G06T 2207/30016* (2013.01); *G06T 2207/30096* (2013.01); *G06T 2207/30101* (2013.01); *G06T 2207/30204* (2013.01)

(56) References Cited

U.S. PATENT DOCUMENTS

| | | | |
|---|---|---|---|
| 6,724,922 B1 | 4/2004 | Vilsmeier | |
| 6,785,572 B2 | 8/2004 | Yanof | |
| 6,919,867 B2 | 7/2005 | Sauer | |
| 7,097,357 B2 | 8/2006 | Johnson et al. | |
| 7,491,198 B2 | 2/2009 | Kockro | |
| 7,892,165 B2 | 2/2011 | Nakamura | |
| 8,010,181 B2 | 8/2011 | Smith et al. | |
| 8,073,528 B2 | 12/2011 | Zhao et al. | |
| 8,211,020 B2 | 7/2012 | Stetten et al. | |
| 8,251,893 B2 | 8/2012 | Yamamoto et al. | |
| 8,398,541 B2 | 3/2013 | DiMaio et al. | |
| 2001/0039421 A1* | 11/2001 | Heilbrun | A61B 5/06 606/130 |
| 2005/0215879 A1 | 9/2005 | Chuanggui | |
| 2006/0142657 A1* | 6/2006 | Quaid | A61B 17/1764 600/424 |
| 2006/0173356 A1 | 8/2006 | Feilkas | |
| 2006/0293557 A1* | 12/2006 | Chuanggui | A61B 90/36 600/101 |
| 2007/0219639 A1* | 9/2007 | Otto | A61F 2/38 623/20.19 |
| 2007/0270685 A1* | 11/2007 | Kang | A61B 17/1764 600/424 |
| 2008/0123910 A1 | 5/2008 | Zhu | |
| 2008/0201016 A1 | 8/2008 | Finlay | |
| 2008/0243142 A1 | 10/2008 | Gildenberg | |
| 2008/0262297 A1 | 10/2008 | Gilboa et al. | |
| 2011/0178394 A1* | 7/2011 | Fitzpatrick | G06T 7/0028 600/424 |
| 2011/0306986 A1 | 12/2011 | Lee | |
| 2011/0320153 A1* | 12/2011 | Lightcap | A61B 34/20 702/94 |
| 2012/0109150 A1* | 5/2012 | Quaid | G06F 19/00 606/130 |
| 2013/0094742 A1 | 4/2013 | Feilkas | |
| 2013/0204287 A1 | 8/2013 | Mark et al. | |
| 2014/0171873 A1 | 6/2014 | Mark | |

FOREIGN PATENT DOCUMENTS

| | | |
|---|---|---|
| EP | 1599148 B1 | 4/2011 |
| EP | 2641561 | 9/2013 |
| GB | 2472066 A | 1/2011 |
| JP | 2006149560 | 6/2006 |
| JP | 2013031660 A | 7/2012 |
| JP | 2013252452 A | 12/2013 |
| KR | 100956762 | 5/2010 |
| WO | 2005074303 A1 | 8/2005 |
| WO | 2010140074 | 12/2010 |

OTHER PUBLICATIONS

International Search Report (PCT/CA 2014/050266) dated Jul. 16, 2014.
Written Opinion (PCT/CA 2014/050266 ) dated Jul. 16, 2014.
The Silent Loss of Navigation Accuracy; Research-Human-Clinical Studies; vol. 72, No. 5, May 2013, pp. 796-807.
European Search Report from EP2967297 dated Dec. 19, 2016.

* cited by examiner

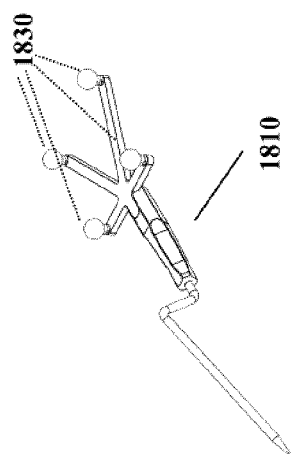

SYSTEM AND METHOD FOR DYNAMIC VALIDATION, CORRECTION OF REGISTRATION FOR SURGICAL NAVIGATION

CROSS-REFERENCE TO RELATED U.S. APPLICATIONS

This application is a National Phase application claiming the benefit of the international PCT Patent Application No. PCT/CA2014/050266, filed on Mar. 14, 2014, in English, which claims priority to U.S. Provisional Application No. 61/799,735, titled "SYSTEM AND METHOD FOR DYNAMIC VALIDATION AND CORRECTION OF REGISTRATION, AND RECOVERY OF LOST REFERENCE, FOR SURGICAL NAVIGATION" and filed on Mar. 15, 2013, the entire contents of which are incorporated herein by reference.

This application claims priority to U.S. Provisional Application No. 61/801,530, titled "SYSTEMS, DEVICES AND METHODS FOR PLANNING, IMAGING, AND GUIDANCE OF MINIMALLY INVASIVE SURGICAL PROCEDURES" and filed on Mar. 15, 2013, the entire contents of which are incorporated herein by reference.

This application claims priority to U.S. Provisional Application No. 61/818,280, titled "SYSTEMS, DEVICES AND METHODS FOR PLANNING, IMAGING, AND GUIDANCE OF MINIMALLY INVASIVE SURGICAL PROCEDURES" and filed on May 1, 2013, the entire contents of which are incorporated herein by reference.

This application claims priority to U.S. Provisional Application No. 61/800,155, titled "PLANNING, NAVIGATION AND SIMULATION SYSTEMS AND METHODS FOR MINIMALLY INVASIVE THERAPY" and filed on Mar. 15, 2013, the entire contents of which are incorporated herein by reference.

This application claims priority to U.S. Provisional Application No. 61/924,993, titled "PLANNING, NAVIGATION AND SIMULATION SYSTEMS AND METHODS FOR MINIMALLY INVASIVE THERAPY" and filed on Jan. 8, 2014, the entire contents of which are incorporated herein by reference.

FIELD

The present disclosure relates to a system and method for dynamic validation and correction of registration, and recovery of lost reference, for surgical navigation during operations.

BACKGROUND

During a navigated surgical procedure a surgeon typically needs to correlate the position of previously acquired imaging data (in three dimensions), that have been obtained from an imaging device or system (for example, ultrasound, CT or MRI data), with the physical position of the patient who is to be operated on. In some systems, for a navigation procedure a handheld instrument may be tracked using a tracking system, and a representation of the instrument's position and orientation may be displayed as an overlay on the three-dimensional imaging data from a scan of the patient's anatomy. To achieve this, a registration is obtained between the coordinate frame of the tracking system for the handheld instrument, the physical location of the patient in physical space, and the coordinate frame of the corresponding image data of the patient. Ensuring that the registration is aligned with and corresponds to the actual physical reality of the procedure is desirable and necessary for maintaining surgeon confidence in the information being presented and in ensuring the navigated procedure is accurately executed.

However, it tends to be difficult to measure and quantify registration accuracy. In the prior art, this accuracy has been reported to a surgeon as a confidence or tolerance number at the time that registration is computed. This was also described by the paper [The Silent Loss of Navigation Accuracy; Research-Human-Clinical Studies; Vol. 72, No. 5, May 2013, pages 796-807]. This number is not indicative of the complexity of registration accuracy, and, more significantly, is not indicative of the fact that accuracy can vary in different parts of the surgical field. Further, this number is used as a one-time accept/reject criterion for the registration—once the registration is accepted typically it is assumed to be correct for the duration of the procedure, or until the surgeon notices that something is significantly misaligned.

With the present state of the art misalignment of the navigation system is difficult to identify as a typical system only presents a virtual representation of the OR procedure, and as such it cannot be readily contrasted to the actual physical state of the OR at a given time. Currently, for a surgeon to measure registration accuracy during a procedure he or she typically locates the tool relative to an identifiable location on the actual patient anatomy while noting the degree to which the location of the virtual tool is displaced from the same location relative to the virtualized patient anatomy, where such virtual tool is displayed as an overlay on the three-dimensional imaging data from a scan of the patient's anatomy. Furthermore, once a registration misalignment is noticed, correcting for the error tends to be difficult, and often not achievable. Additionally, non-uniform displacement of tissue during a procedure also tends to mean that global corrections are not possible.

SUMMARY

This application describes a system and method for validating registrations, and detecting and correcting registration.

An embodiment disclosed herein provides a method of confirmation of correct registration between one or more previously registered virtual objects in a coordinate frame of a surgical navigation system (which is located in an operating room in which a medical procedure is to be performed) and intra-operatively acquired imaging during the medical procedure in the coordinate frame of the surgical navigation system. Wherein a previously registered virtual object may be a computed tracked instrument visualization, or other computed tracked real object visualization. The surgical navigation system includes a tracking mechanism. The method include displaying intra-operatively acquired imaging of a surgical field containing one or more real objects corresponding to the one or more virtual objects, the surgical field containing a pre-selected number of landmarks in fixed and known locations with respect to the one or more real objects, with the landmarks being tracked by the tracking mechanism. The method includes overlaying a virtual image (as generated by a virtual camera) containing the one or more virtual objects previously registered onto the intra-operatively acquired imaging and detecting for any misalignment or non-concordance between any one of the one or more previously registered virtual objects contained in the virtual image and its corresponding real object contained in the intra-operatively acquired imaging, wherein a presence of misalignment or any non-concordance is indicative of a registration error.

An embodiment disclosed herein is a system for confirmation of correct registration between one or more previously registered virtual objects and intra-operatively acquired imaging during a medical procedure. The systems comprises a surgical navigation system having a coordinate frame of reference and including a tracking mechanism. The system further comprises a computer control system which includes a computer processor, and a storage device and a visual display both connected to the computer processor. The storage device has stored therein a visualization of one or more previously registered virtual objects in the coordinate frame of reference of the surgical navigation system. The system includes at least one sensor for acquiring intra-operative imaging of a surgical field during the medical procedure in which the surgical field contains one or more real objects corresponding to the one or more virtual objects and a pre-selected number of landmarks in known locations with respect to the one or more real objects. The landmarks and the at least one sensor are tracked by the tracking mechanism in the coordinate frame of the surgical navigation system. The computer processor is programmed with instructions to receive and display the intra-operatively acquired imaging of the surgical field containing the one or more real objects and to overlay the virtual image containing the one or more virtual objects previously registered onto the intra-operatively acquired imaging and wherein any misalignment or non-concordance between any one of the one or more previously registered virtual objects contained in the virtual image and its corresponding real object contained in the intra-operatively acquired imaging is indicative of a registration error between the virtual object and its corresponding real object in said coordinate frame of said surgical navigation system.

In an embodiment, the described system and method can also provide corrections based on the difference between local tissue characteristics and virtual instrument representations at the location that the surgeon is focusing on and a live video stream of the surgical field to immediately visualize (and optionally automatically or manually correct for) any difference between the expected (as calculated through a registration) and actual positions of tracked instruments and imaged patient tissue, which tends to achieve local, immediate, corrections of registration in an intuitive way.

A further understanding of the functional and advantageous aspects of the invention can be realized by reference to the following detailed description and drawings.

In an embodiment a method of confirmation of registration between one or more previously registered virtual objects in a common coordinate frame of a surgical navigation system and an operating room in which a medical procedure is to be performed, and intra-operatively acquired imaging during said medical procedure in said common coordinate frame, said surgical navigation system including a tracking system, the method comprising: a) displaying intra-operatively acquired imaging of a surgical field containing one or more real objects corresponding to said one or more previously registered virtual objects, the real objects being tracked by the tracking system; b) overlaying a virtual image containing the one or more previously registered virtual objects onto the intra-operatively acquired imaging, from the point of view of the intra-operatively acquired imaging; and c) detecting for any misalignment between any one of the one or more previously registered virtual objects contained in the virtual image and its corresponding real object contained in the intra-operatively acquired imaging, wherein a presence of misalignment is indicative of registration error between the virtual object and its corresponding real object.

In yet another embodiment a system for confirmation of correct registration between one or more previously registered virtual objects and intra-operatively acquired imaging during a medical procedure, comprising: a) a surgical navigation system having a coordinate frame and including a tracking mechanism; b) a computer control system including a computer processor, a storage device and a visual display both connected to said computer processor, said storage device having stored therein a computed tracked instrument visualization of one or more previously registered virtual objects in said coordinate frame of reference of said surgical navigation system; c) at least one sensor for acquiring intra-operative imaging of a surgical field during the medical procedure, said surgical field containing one or more real objects corresponding to said one or more virtual objects; and d) said computer processor being programmed with instructions to receive and display said intra-operatively acquired imaging of the surgical field and to overlay a virtual image from the point of view of the virtual camera onto the intra-operatively acquired imaging, wherein any misalignment between any one of the one or more previously registered virtual objects contained in the virtual image and its corresponding real object contained in the intra-operatively acquired imaging is indicative of a registration error between the virtual object and its corresponding real object.

BRIEF DESCRIPTION OF THE DRAWINGS

Embodiments disclosed herein will be more fully understood from the following detailed description thereof taken in connection with the accompanying drawings, which form a part of this application, and in which:

FIG. 18 (b) shows a diagram of a medical pointer tool with a template and optical tracking assembly.

DETAILED DESCRIPTION

Various apparatuses or processes will be described below to provide examples of embodiments of the invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention.

Furthermore, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Furthermore, in the following passages, different aspects of the embodiments are defined in more detail. In particular, any feature indicated as being preferred or advantageous may be combined with at least one other feature or features indicated as being preferred or advantageous.

As used herein, the phrase "intra-operatively acquired imaging" refers to images of a medical procedure being performed on an anatomical part. The imaging procedure may include using a sensor to acquire a continuous intra-operatively acquired image stream (i.e. obtained for example by a video camera corresponding to real-time imaging) or an intra-operatively acquired image taken at one or more specific times during the procedure using a sensor other than a video camera, for example a sensor (such as, but not limited to a camera) which is configured to record specific types of images one by one. The present disclosure includes both modalities.

Figure 1:
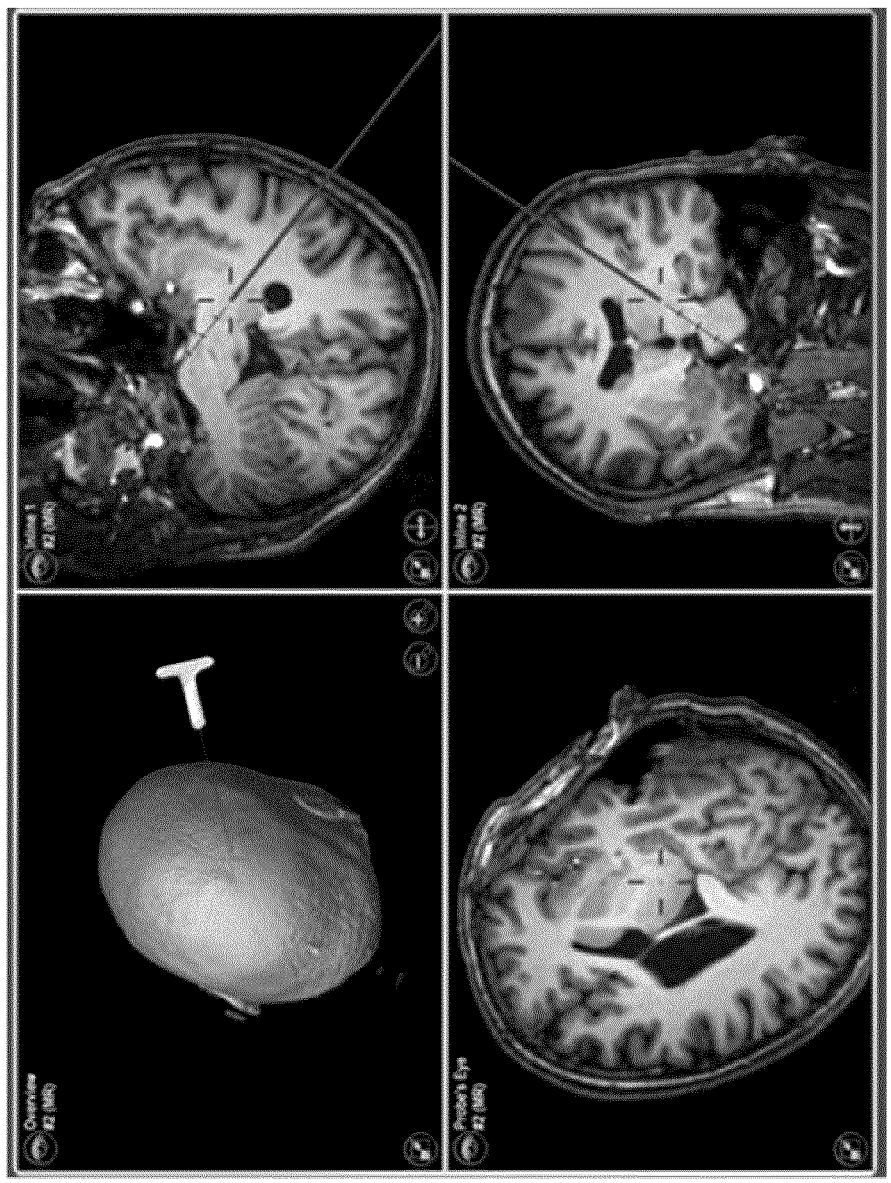
FIG. 1 shows an example of a presently used navigation system that supports minimally invasive surgery.
Figure 2:
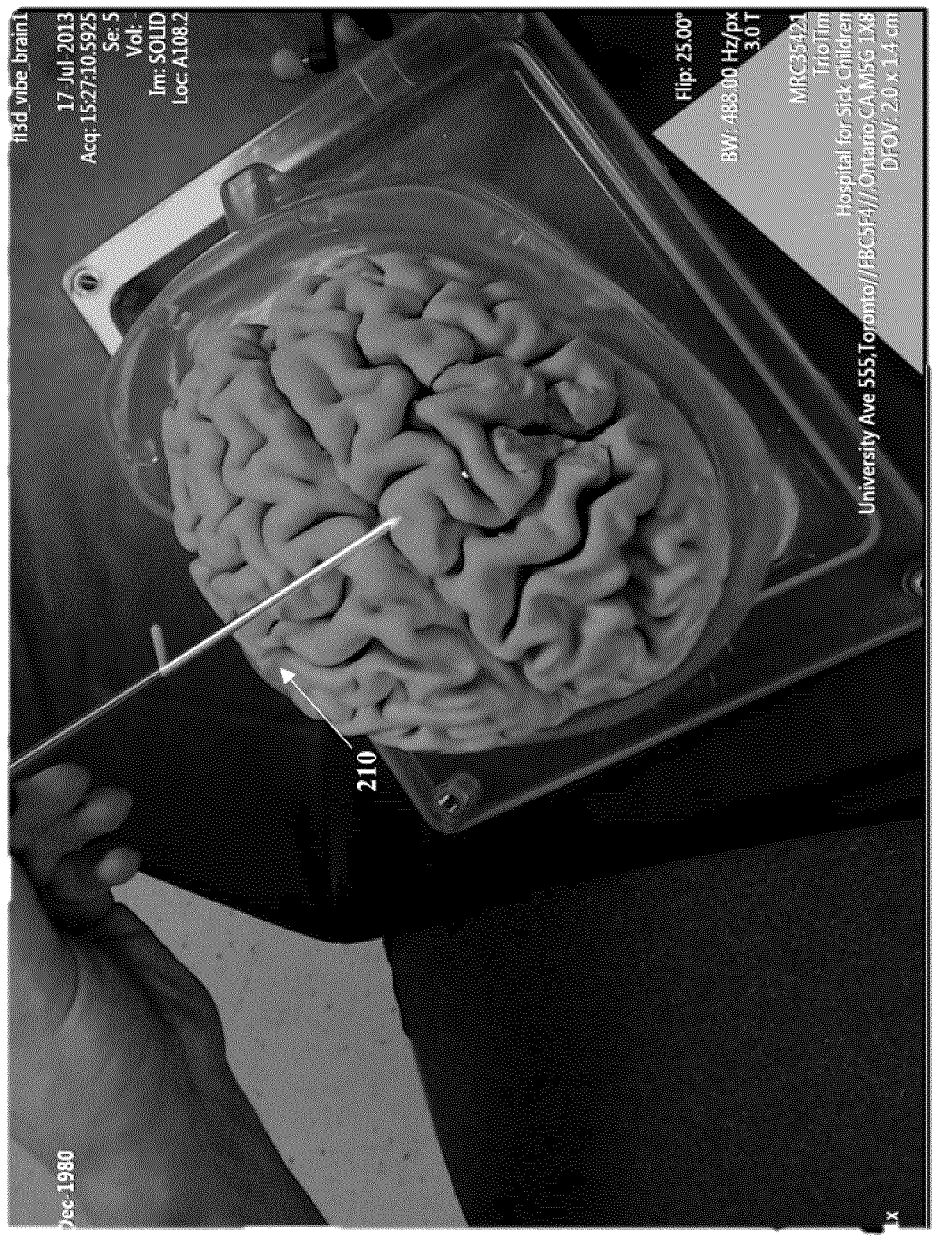
FIG. 2 shows a mock brain and the output of a navigation system showing correct registration of a tool.
Figure 3:
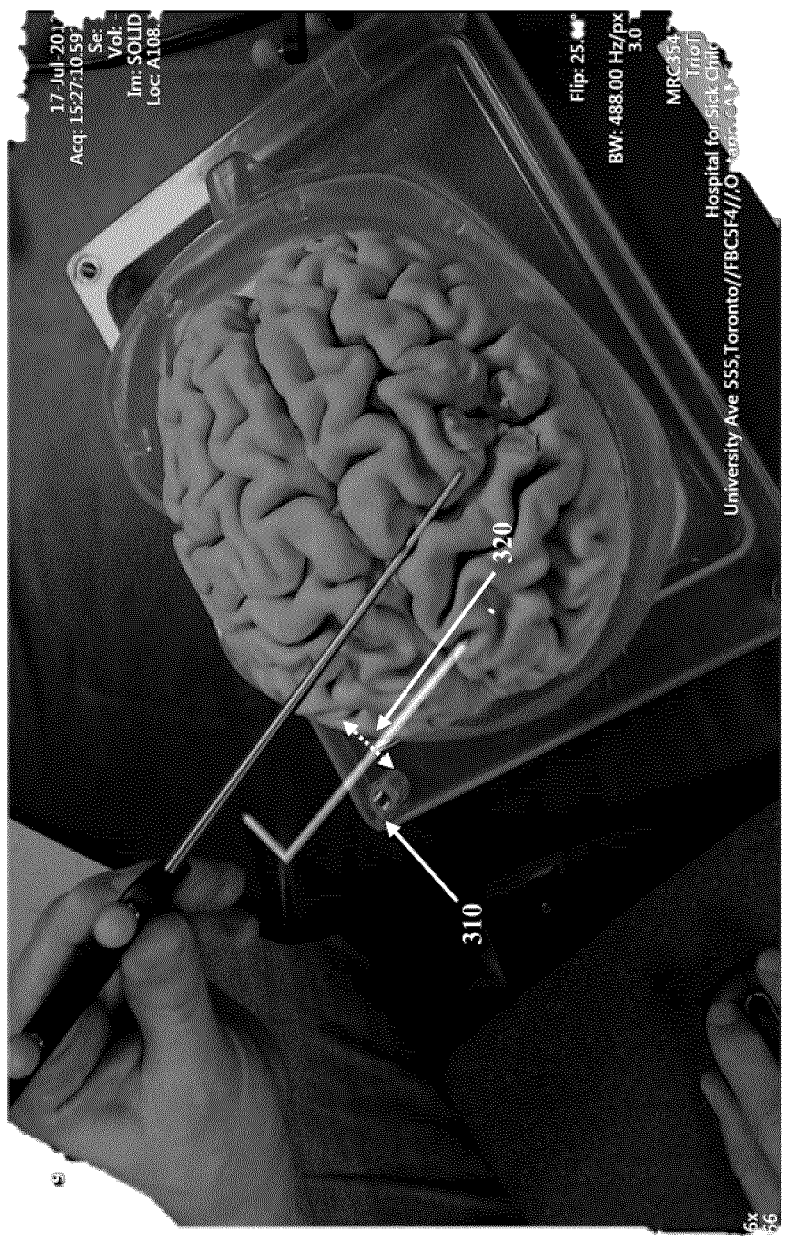
FIG. 3 shows a mock brain and the output of a navigation system showing mis-registration of a tool.

In an embodiment, there is provided a continuously available and real-time confirmation of registration, with an intuitive interface for verification and correction (if necessary). In the embodiment, an overlay of computed tracked instrument visualization and patient imaging information on a video image of the surgical field is provided during a procedure. In FIG. 2 a surgical tool and its virtual representation are shown aligned (210). In this image, any registration errors may be seen and recognized by an observer (such as a surgeon), as a simple misalignment of the computed tracked instrument visualization and the actual physical object seen on the video image. An example of erroneous registration (or mis-registration) is shown in FIG. 3 in which the virtual representation 310 of the surgical tool is seen to be displaced from the actual surgical tool by a distance 320. The surgical instrument(s) may be tracked with one or more sensors which are in communication with one or more transceiver(s) of the tracking systems that receive, record and/or process the information regarding the instrument(s) that the sensor(s) are detecting. The sensors may track, among other things, the spatial position of the instrument(s), including its angle and orientation (i.e. pose).

Figure 17:
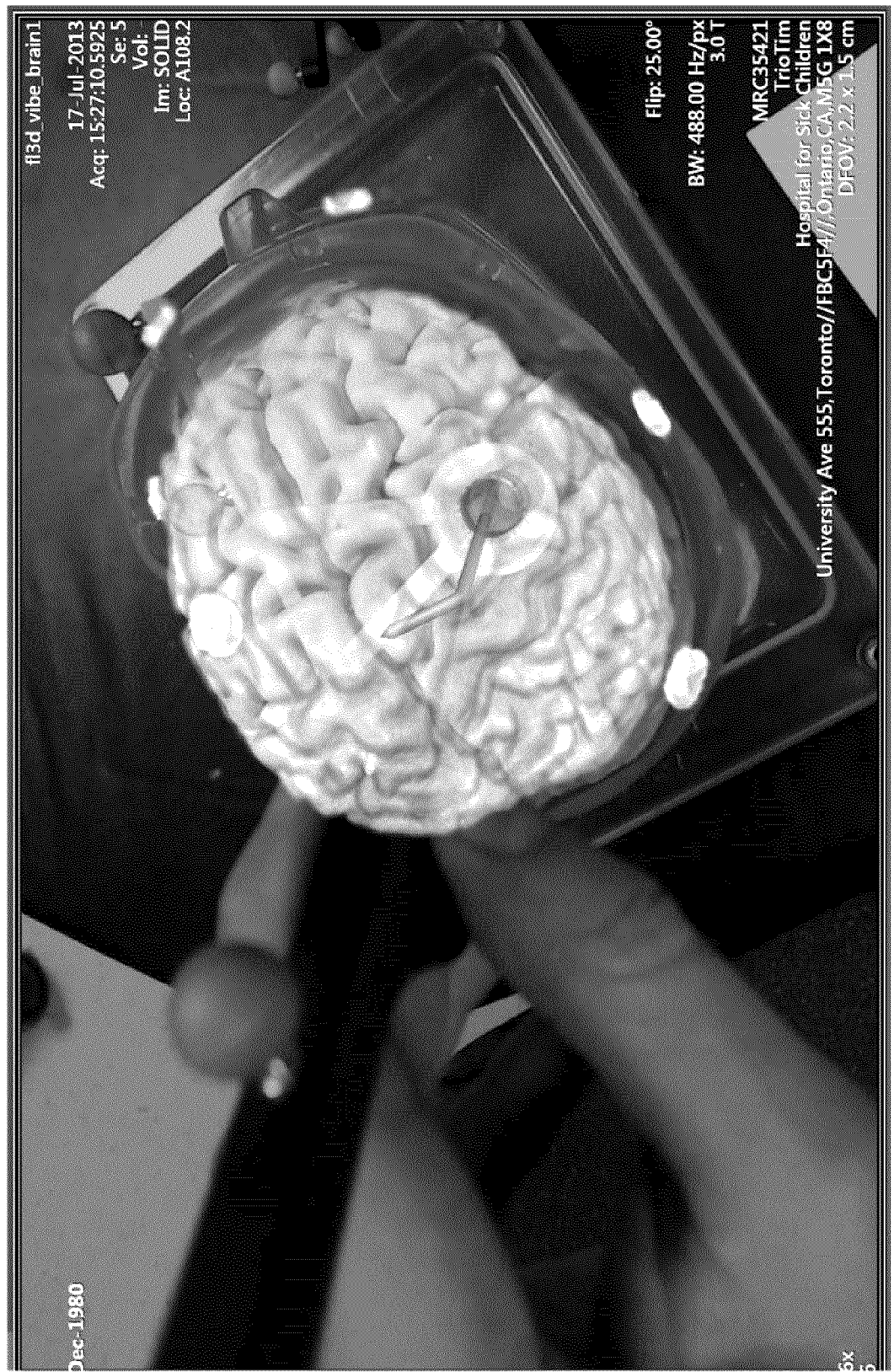
FIG. 17 shows a navigation system screen shot of a mock medical procedure showing real objects overlaid by virtual objects.

Persons skilled in the art will appreciate that being able to visualize a medical instrument when it is within a patient will aid in the improvement of the accuracy of the procedure. This can be seen in FIG. 17 as the instrument may be visualized through the image of a mock patient.

Figure 7:
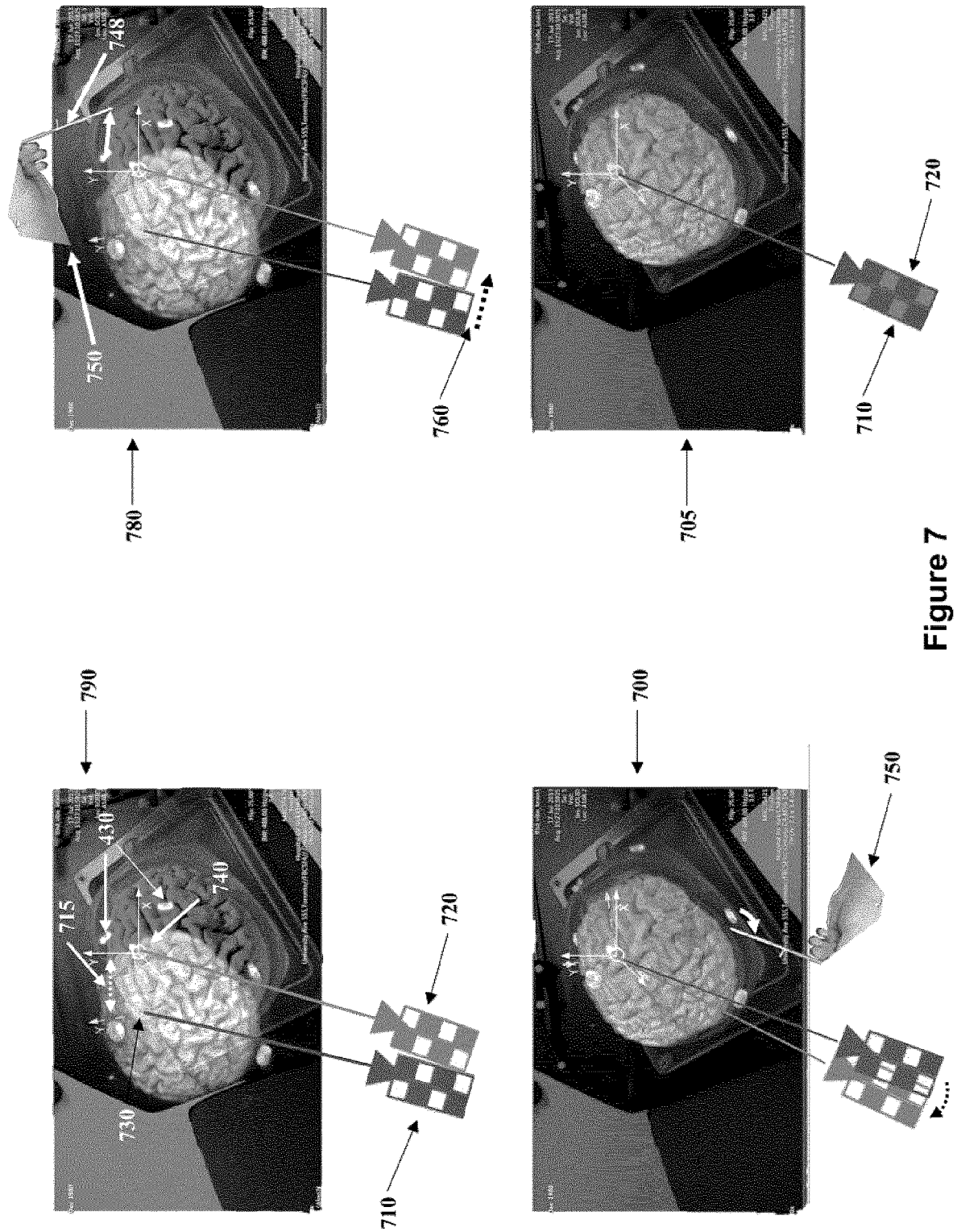
FIG. 7 shows a diagram of the registration process wherein the virtual mock brain is registered with its actual counterpart using touchpoints and fiducials.

Referring to FIG. 7, in an embodiment a coordinate frame (730) of the navigation system may be spatially registered with the coordinate frame (740) of the patient imaging data through the respective alignment of corresponding pairs of virtual and actual points as described below. This procedure results in the formation of a common coordinate frame. In an embodiment shown in FIG. 4 the virtual space markers (420) can be seen on a mock patient's pre-operative MR scan, while the actual space fiducials (1000) corresponding to the virtual space markers can be seen in FIG. 10 on the head of the mock patient. Referring again to FIG. 7 there is shown an embodiment of the registration process in which a virtual camera (710) is aligned with the actual camera (720) for the purposes of rendering a 3D scan of the mock brain such that the rendered position, orientation and size match the image from the actual camera and is overlaid onto the real-time video stream of the surgical area of interest.

A virtual camera is the point and orientation in virtual 3D space that is used as a vantage point from which the entire virtual 3D scene is rendered. The virtual markers are objects within this virtual 3D scene. It is understood that those familiar in the art will recognize this methodology as a standard computer graphics technique for generating virtual 3D scenes.

The present system may be used with any compatible surgical navigation system. A non-limiting example of such a surgical navigation system is outlined in the co-pending U.S. patent application entitled "SYSTEMS AND METHODS FOR NAVIGATION AND SIMULATION OF MINIMALLY INVASIVE THERAPY", U.S. Pat. Publication US20150351860 based on U.S. patent application Ser. No. 14/655,814, which claims the priority benefit of U.S. Provisional Patent Application Ser. Nos. 61/800,155 and 61/924,993, and wherein for the purposes of this present United States Patent Application, the Detailed Description, and Figures of U.S. Pat. Publication US20150351860 are incorporated herein by reference.

Figure 15:
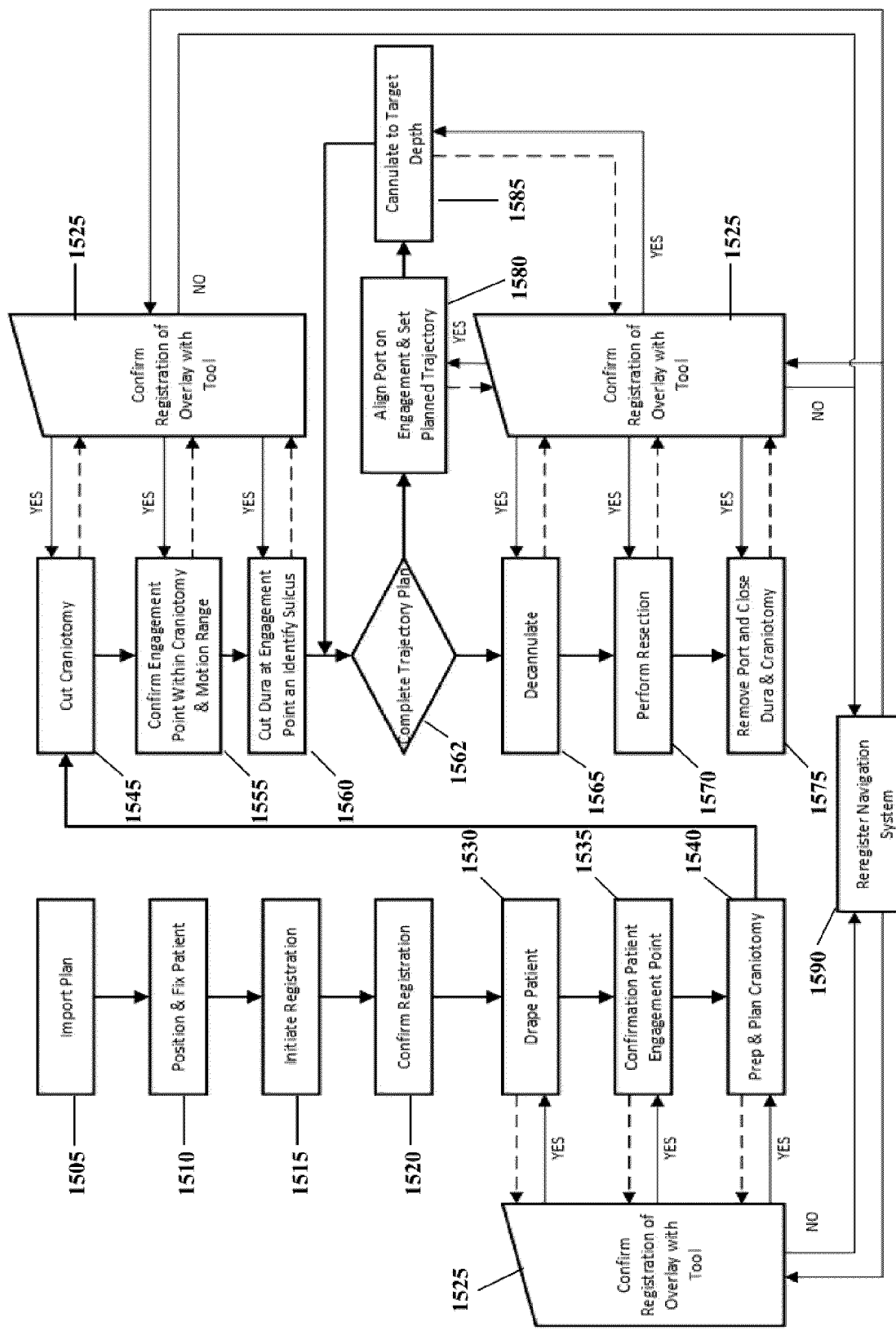
FIG. 15 shows a flow chart showing the steps involved in a port based brain surgery procedure including monitoring of registration.

In an embodiment the validation system is used in a port based surgery the phases of which are depicted in FIG. 15. This flow chart illustrates the steps involved in a port-based surgical procedure using a navigation system. The first step in this surgical procedure involves importing the port-based surgical plan (step 1505) into the navigation system. A detailed description of a process to create and select a surgical plan is outlined in the co-pending "SYSTEM AND METHODS FOR MINIMALLY DU-RING INVASIVE THERAPY" U.S. Pat. Publication US20160070436 based on U.S. patent application Ser. No, 14/769,668, which claims the priority benefit of U.S. Provisional Patent Application Ser. Nos. 61/800,155 and 61/924,993, and wherein for the purposes of this present United States Patent Application, the Detailed Description, claims and Figures of U.S. Pat. Publication US20160070436 are incorporated herein by reference.

Once the plan has been imported into the navigation system (step 1505), the anatomical part of the patient is affixed into position using a head or body holding mechanism. The patient position is also confirmed with the patient plan using the navigation software (step 1510). In this embodiment, the plan is reviewed and the patient positioning is confirmed to be consistent with craniotomy needs. Furthermore, a procedure trajectory may be selected from a list of planned trajectories produced in the planning procedure.

Returning to FIG. 15, the next step is to initiate registration of the patient (step 1515). The phrase "registration" or "image registration" refers to the process of transforming different sets of data into a unitary coordinate system.

Figure 8:
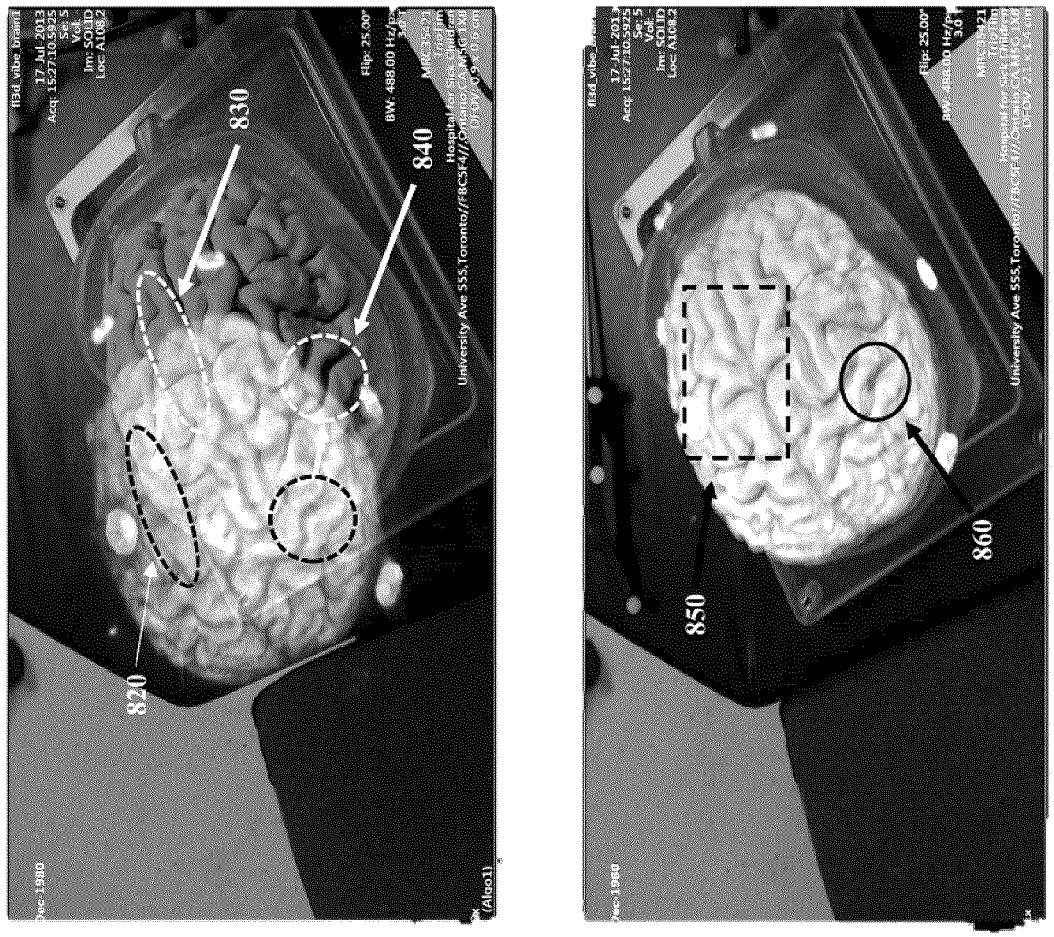
FIG. 8 shows a diagram of the registration process wherein the virtual mock brain is registered with its actual counterpart using pattern recognition.

Those skilled in the art will appreciate that there are numerous registration techniques available and one or more of them may be used in the present application such as the one described in this disclosure and shown in FIG. 7. Non-limiting examples include intensity-based methods which compare intensity patterns between images via correlation metrics, while feature-based methods find correspondence between images using features such as points, lines, and contours as further described below and as shown in FIG. 8. Image registration algorithms may also be classified according to the transformation models they use to relate the target image space to the reference image space.

Figure 16:
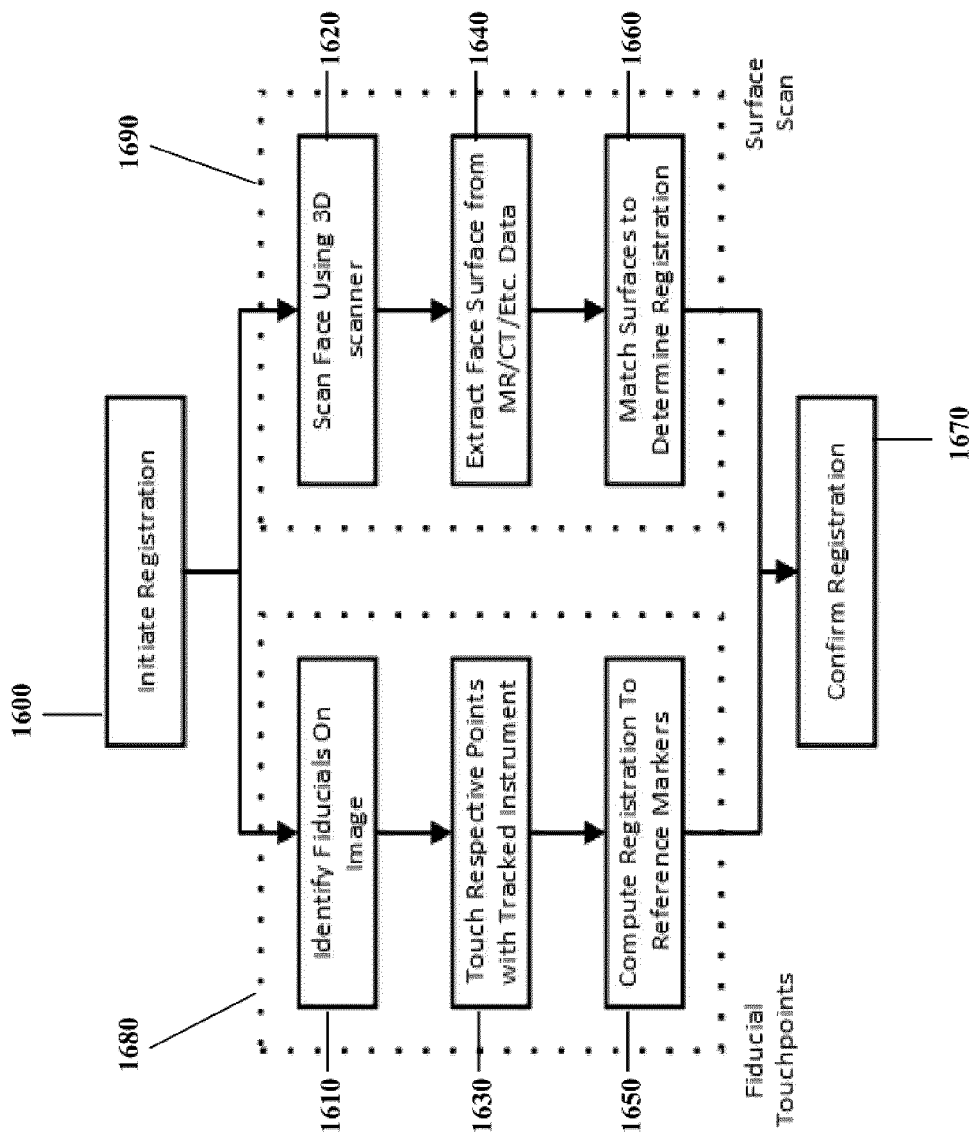
FIG. 16 shows a flow chart describing two possible registration methods.
Figure 18:
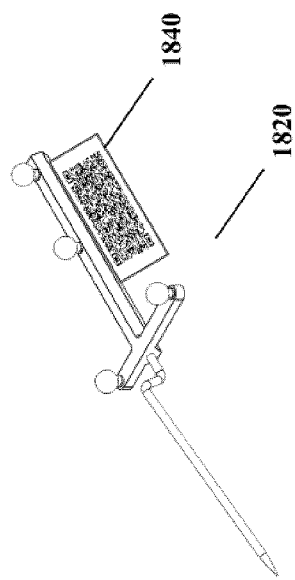
FIG. 18 (a) shows a diagram of a medical pointer tool with an optical tracking assembly.

FIG. 16 is a flow chart illustrating the further processing steps involved in registration as outlined in FIG. 15. In this exemplary embodiment, registration can be completed using a fiducial touchpoint method (1680) in which the location of touchpoints are registered using a pointing tool. The fiducial touchpoint method (1680) is described further below and is shown in FIG. 7. Two non-limiting examples of pointing tools used in a fiducial touchpoint method are shown in FIG. 18. Pointing tool (1820) is shown having a template, and pointing tool (1810) is shown without a template, as further described below.

Registration can also be completed by conducting a surface scan procedure shown generally at (1690) in FIG. 16. Typically for a navigated brain surgical procedure the first step (1620) of a surface scan involves scanning the face using a laser or other scanning device. The next step is to extract the face surface from MR/CT data (step 1640). Finally, registration is performed using a surface-matching method.

As described herein the overlay of registered virtual and corresponding real objects in the surgical suite displayed by the navigation system allows for the identification of misregistration arising between a virtual object and its corresponding real object in the surgical suite. As shown in FIG. 15 in each step of the procedure following confirmation of registration step (1520) the user (surgeon or other member of the surgical team) may readily determine the degree of accuracy of registration, as the user is permitted to confirm registration in step (1525) of the virtual and actual objects in the OR before moving forward to the next step in the medical procedure. However if at any time a discrepancy, for example as seen at (320) in FIG. 3, between the virtual overlaid object and actual object is recognized the system may be re-registered (1590) using one of the embodiments described herein.

The subsequent steps after initial registration (1515) and confirmation of registration (1520) in a port-based procedure are further outlined in FIG. 15 and are further described below.

Initial registration typically has occurred before the patent is draped (1530). Draping typically involves covering the patient and surrounding areas with a sterile barrier to create and maintain a sterile field during the surgical procedure. The purpose of draping is to eliminate the passage of microorganisms (i.e., bacteria) between non-sterile and sterile areas.

Upon completion of draping (step 1530), the next step is to confirm patient engagement points (step 1535) and then prepare and plan the craniotomy (step 1540).

Upon completion of the prep and planning of the craniotomy step (step 1540), the next step is to cut craniotomy (step 1545) where a bone flap may be removed from the skull to access the brain. The above steps of draping, and performing craniotomy, are known in the art to add to registration inaccuracy.

The next step is to confirm the engagement point and the motion range of the port (step 1555), and once this is confirmed the procedure typically advances to the next step of cutting the dura at the engagement point and identifying the sulcus (step 1560).

Thereafter, the cannulation process may be initiated (step 1562). Cannulation involves inserting a port into the brain, typically along a sulcus path as identified in step 1560 using an obturator (introducer). Cannulation may be an iterative process that involves repeating the steps of aligning the port, setting the planned trajectory (step 1580), and then cannulating to a target depth (step 1585), until the complete trajectory plan is executed (step 1562).

The surgery then proceeds (step 1565) by removing the obturator (introducer) from the port allowing access to the surgical site of interest. The surgeon then perform treatment at the distal end of the port, which may involve resection (step 1570) to remove part of the brain and/or tumor of interest. Lastly, the surgeon typically remove the port, close the dura and close the craniotomy (step 1575).

Figure 19:
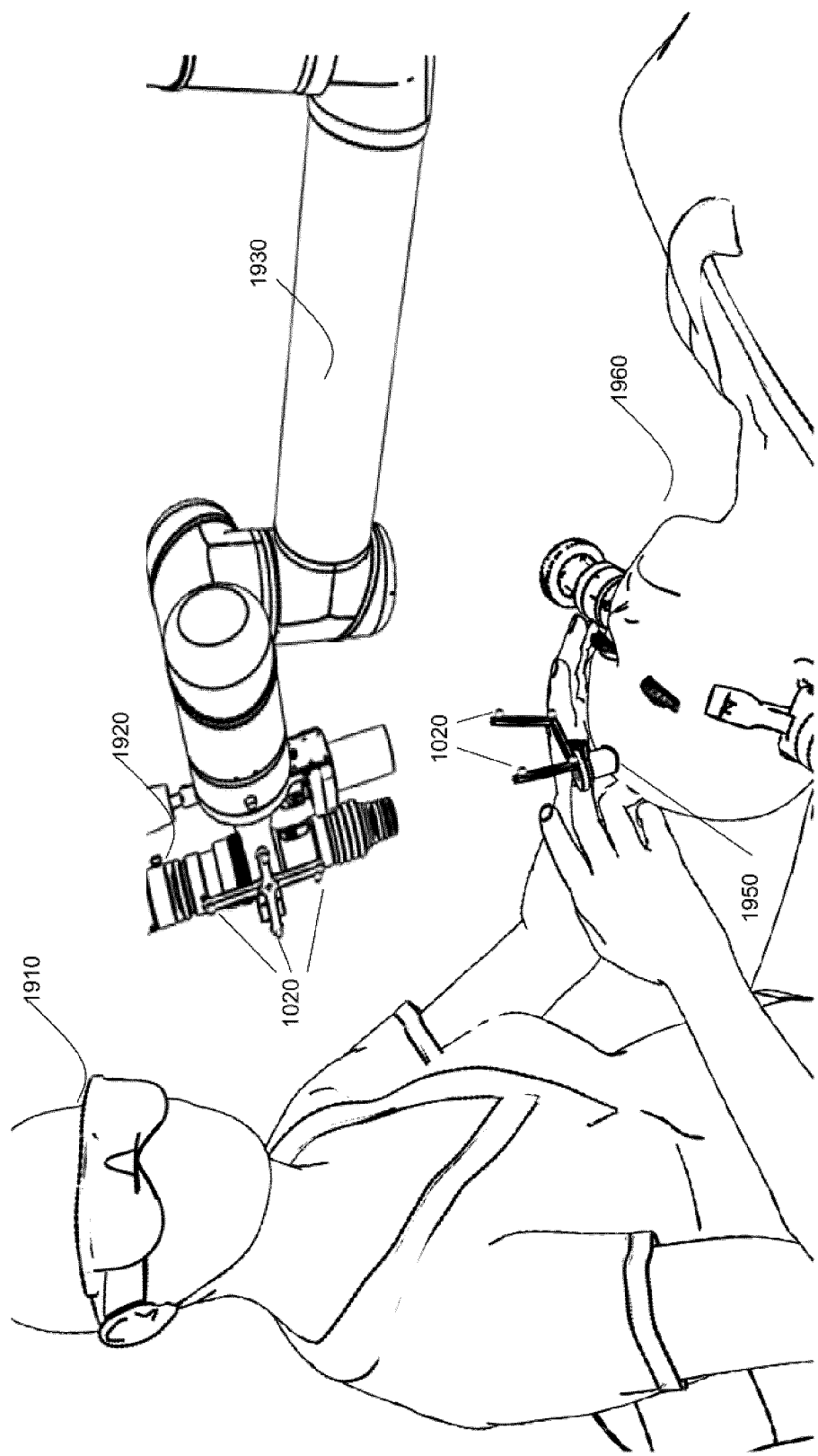
FIG. 19 shows a diagram of a port based neurosurgery.

FIG. 19 is an illustration showing tracked tools in a port-based surgical procedure. In FIG. 19, surgeon (1910) is resecting a tumor in the brain of a patient (1960), through port (1950). External scope (1920), attached to mechanical arm (1930), is typically used by the surgeon to enhance visibility of the brain at the distal end of the port (1950). The external scope (1920) may be zoomed-in or zoomed-out, and its output depicted on a visual display (not shown) which may be overlayed with the virtual image of the actual objects contained in the field of view of the external scope (1920), allowing for the validation of registration as described herein.

Active or passive fiduciary markers (1020) may be placed on the port (1950) and/or imaging sensor (same as 720 in FIG. 7) to deteremine the locaton of these tools by the tracking camera (1110) and navigation system. These markers (1020) may be reflective spheres configured to be seen by the stereo camera of the tracking system to provide identifiable points for tracking. A tracked instrument in the tracking system is typically defined by a grouping of markers (1830), which identify a volume in the tracking system, and are used to determine the spatial position and pose of the volume of the tracked instrument in three dimensions. Typically, in known exemplary tracking systems a minimum of three spheres are required on a tracked tool to define the instrument, however it is known in the art that use four markers (1830) is preferred.

Markers (1020) may be arranged statically on the target on the outside of the patient's body or connected thereto. Tracking data of the markers acquired by the stereo camera are then logged and tracked by the tracking system. An advantageous feature is the selection of markers that can be segmented easily by the tracking system against background signals. For example, infrared (IR)-reflecting markers (1020) and an IR light source from the direction of the stereo camera can be used. Such tracking system is known, for example, such as the "Polaris" system available from Northern Digital Inc.

In a preferred embodiment, the navigation system may utilize reflective sphere markers in combination with a stereo camera system, to determine spatial positioning and pose of the medical instruments and other objects within the operating theater. Differentiation of the types of medical instruments and other objects and their corresponding virtual geometric volumes could be determined by the specific orientation of the reflective spheres relative to one another giving each virtual object an individual identity within the navigation system. This allows the navigation system to identify the medical instrument or other object and its corresponding virtual overlay representation (i.e. the correct overlay volume) as seen as (310) in FIG. 3. The location of the markers also provide other useful information to the tracking system, such as the medical instrument's central point, the medical instrument's central axis and orientation, and other information related to the medical instrument. The virtual overlay representation of the medical instrument may also be determinable from a database of medical instruments.

Other types of markers that could be used would be RF, EM, LED (pulsed and un-pulsed), glass spheres, reflective stickers, unique structures and patterns, where the RF and EM would have specific signatures for the specific tools they would be attached to. The reflective stickers, structures and patterns, glass spheres, LEDs could all be detected using optical detectors, while RF and EM could be picked up using antennas. Advantages to using EM and RF tags would include removal of the line-of-sight condition during the operation, whereas using an optical-based tracking system removes the additional noise and distortion from environmental influences inherent to electrical emission and detection systems.

In a further embodiment, 3-D design markers could be used for detection by an auxiliary camera and/or optical imaging system. Such markers could also be used as a calibration pattern to provide distance information (3D) to the optical detector. These identification markers may include designs such as concentric circles with different ring spacing, and/or different types of bar codes. Furthermore, in addition to using markers, the contours of known objects (i.e., side of the port) could be made recognizable by the optical imaging devices through the tracking system.

In another further embodiment, the medical instrument may be made or configured with an additional protrusion or feature that would not normally be obscured during a procedure, so that such protrusion or feature would typically be visible to the optical sensor during the procedure. Having such feature or protrusion on a tool would enable a verification of registration despite the fact that other portions of the tool may be obscured by patient anatomy, or other objects. As such, in such an embodiment it would be possible to verify registration without having to remove the tool from the patient.

Figure 4:
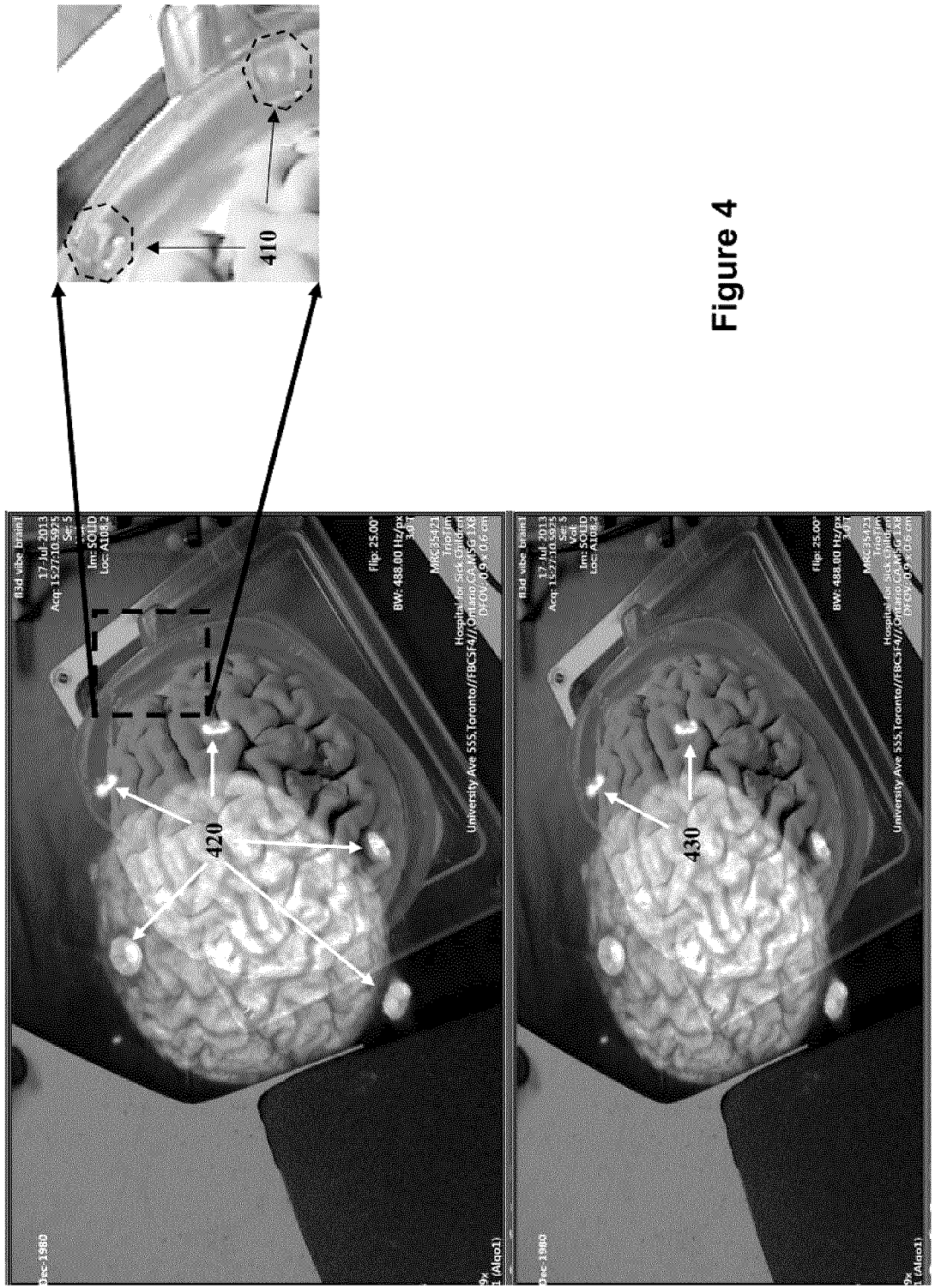
FIG. 4 shows a navigation system diagram including fiducial touchpoints used for registration of the mock head and brain.
Figure 10:
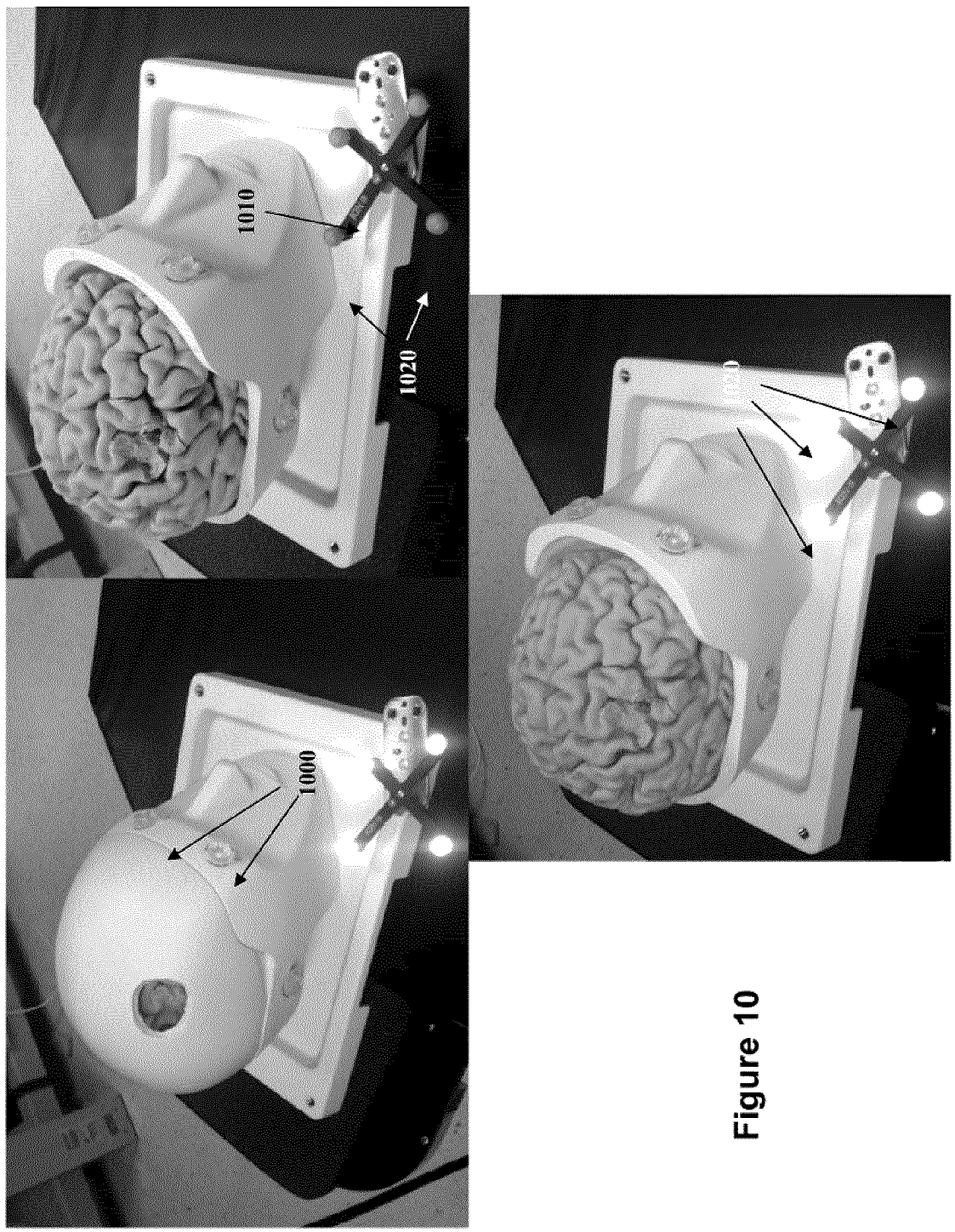
FIG. 10 shows a diagram of a mock brain, a mock head, a mock head holder, and tracking marker reference affixed to the mock head holder in a known and fixed location.

Referring to FIG. 7, in use of the navigation system, its tracking system will provide the navigation system a coordinate frame (740), containing the actual spatial locations of the tracked elements in the operating room, and their spatial relation to one another. Examples of such tracked elements would be the surgical real-time imaging camera (720), which may be a moveable camera used for visualization of the surgical area of interest, a surgical volume of interest such as a brain, and/or medical instruments. A 3D virtual volume representing pre-operative image data (510) (shown in FIG. 5) of patient anatomy is also provided to the navigation system. In an embodiment, the virtual volume is acquired using a patient with attached fiducials (1000, as shown in FIG. 10). The fiducials (1000) remain attached in place on the patient (or else their locations have been marked on the patient (as shown in FIG. 4 at (410)) in a manner which persists through the registration step) in order to register the pre-operative imaging data with the patient in the operating room. This is illustrated in FIG. 4, which shows two virtual fiducial markers (430) within a mock patient's head scan being in the same position relative to the virtual mock brain having the actual fiducial markers (1000) as seen in FIG. 10). The spatial correspondence between the actual fiducials and the virtual fiducials permits their respective coordinate frames to be aligned, which allows for an accurate overlay of virtual image data onto the actual image data. The overlay is achieved by combining video from a virtual camera (710) (shown in FIG. 7) depicting the virtual operating room (OR) surgical field and video from an actual surgical imaging camera (720) (FIG. 7) depicting the actual OR surgical field. To obtain an accurate overlay, the two cameras (710 and 720) must be coincidentally aligned and have the same optical properties. Hence the alignment of virtual camera (710) in the navigation system coordinate frame (730) is constrained to be equivalent to the alignment of the actual camera (720), relative to operating room coordinate frame (740), and have the same optical properties as the actual camera (720), namely, the same field-of-view, aspect ratio, and optical distance. This is accomplished using the navigation system. Given an initial discrepancy or spatial separation (715) between coordinate frames (730 and 740), a tracked pointer (748) controlled by a user (750) can be used to confirm the spatial location of the actual fiducials in virtual space as depicted in picture frame (780) in the upper right hand side in FIG. 7.

In general, each time a point is identified, the virtual and actual coordinate frames, (730) and (740) respectively, become more accurately aligned. For example, as the tip of the pointer (748) in FIG. 7 indicates the spatial position of a fiducial in actual space (located above the left eyebrow of the mock patient), its virtual counterpart fiducial aligns with it resulting in the navigation system coordinate frame (730) to transform (760) and align its origin with the operating room coordinate frame (740). This also results in the two cameras (710) and (720) realigning themselves accordingly. It should be noted that the relative shift in alignment of cameras (710) and (720), shown between diagrams (790) and (700), is proportional to the shift between the virtual alignment of the overlay on the actual image data between (790) and (700). However, given that the coordinate frames (730) and (740) respectively are still rotationally misaligned, as can be seen in the bottom left picture frame (700) in FIG. 7, the alignment process is repeated and another point is registered. In this iteration the fiducial being aligned is located near the right ear of the mock patient and this causes a rotation of the coordinate frame (730) resulting in it and the coordinate frame (740) to better coincidently align. Repetition of the above steps results in the production of a common coordinate frame, and accurate registration, as can be seen in diagram (705) (in the lower right hand side of FIG. 7) which shows the accurate overlay of the virtual and mock brain as a result of the coincident alignment of the virtual and actual cameras (710) and (720), respectively.

Figure 5:
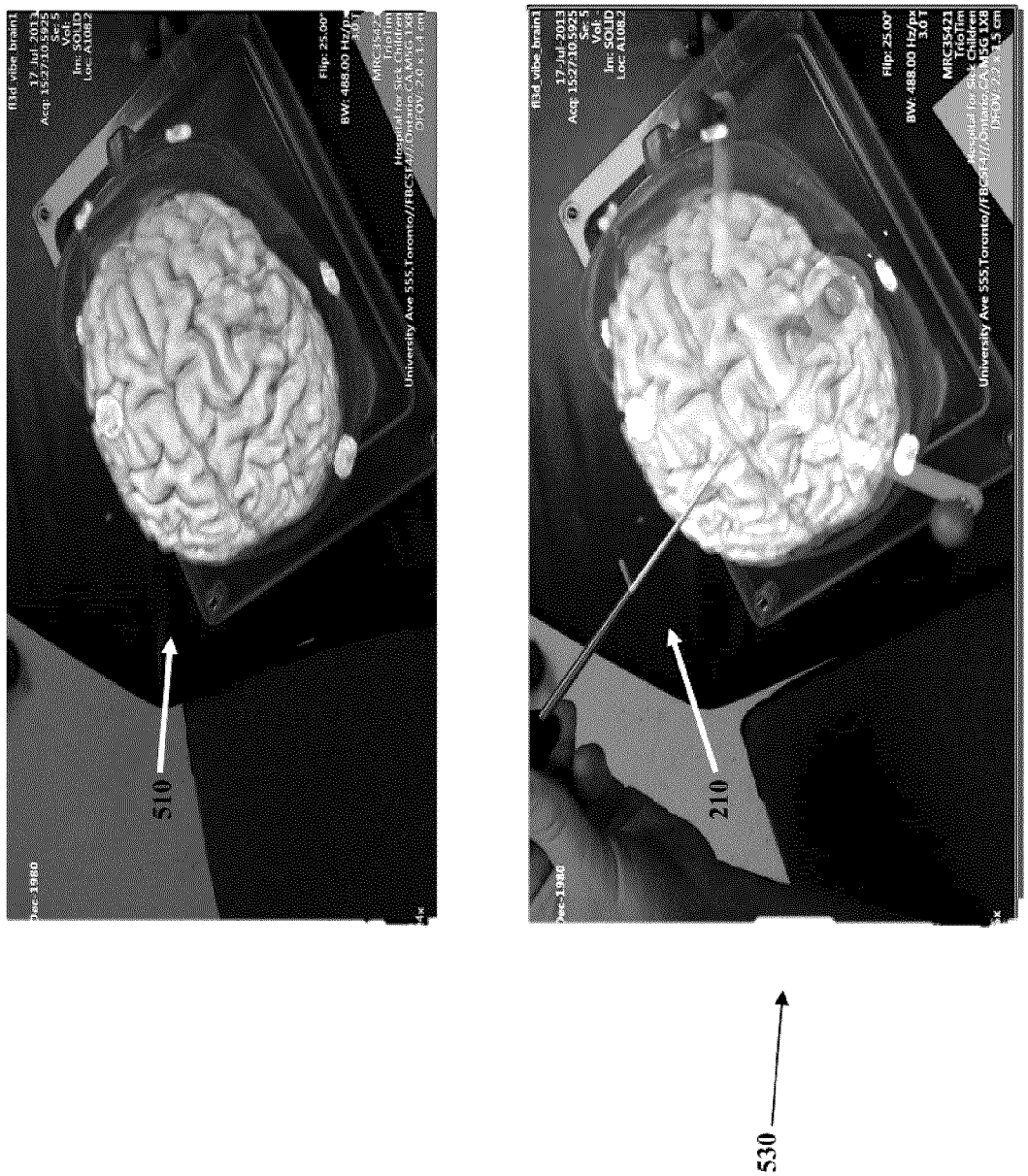
FIG. 5 shows a navigation system diagram showing correct registration in a mock surgery, of an overlay of the tracked virtual objects and their actual counterparts in real time and actual space.
Figure 11:
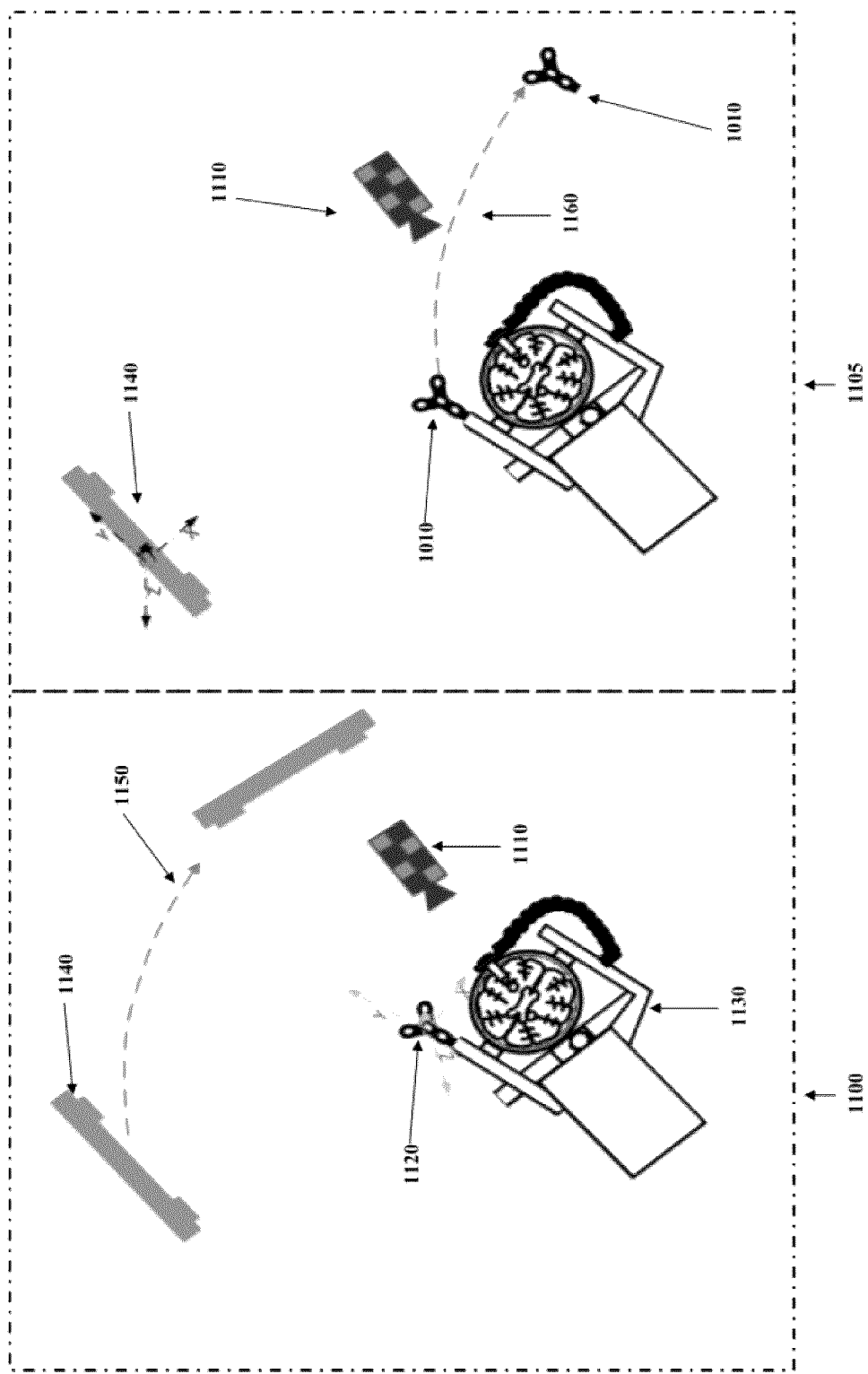
FIG. 11 shows a diagram of both the "camera fixed" and "reference fixed" modes of the navigation system.

As shown in FIG. 11, a tracking camera 1140 (i.e., an optical measurement system that measure the 3D positions of either active or passive markers or landmarks) is placed in a known position relative to an immobilized patient. As shown in FIG. 5, a computed image (510) from mock patient image data that has been previously obtained or is being obtained (intra-operatively, including by way of x-ray, MRI, CT, ultrasound, and/or PET, among other modalities) and/or the virtual representation of a medical instrument (210), may then be overlaid onto the video image, as shown in picture frame (530). It is noted that video sensor (1110) as seen in FIG. 11 is a camera used for visualization of the surgical area of interest (for example which may be an external scope, or wide field camera), whereas tracking camera (1140) is a 3D tracking sensor (a non-limiting example being a "Polaris Spectra" camera).

In an embodiment, any tracked medical instrument(s) and 3D MR image data is computed for display as an overlay in the live video image feed, positioned relative to the registration transform, (for example a data overlay corresponding to an anatomical part (510), and the anatomical part). This would show alignment of the computed display with the video image of both the instrument(s) and the contours of the anatomical data if registration is correct, as shown in the bottom image (530) of FIG. 5. Any misalignment between the overlay and the actual video image of the tool would be immediately noticeable as a mis-registration, and indicate an error in the tracking system registration. This can be seen as the displacement (320) between the projected (overlaid) tool representation and the actual tool in FIG. 3 discussed above. Further, any misalignment between the overlay and the actual video image of an anatomical part would be immediately noticeable as a mis-alignment, and indicate either an error in the tracking system registration or a deformation of the anatomical tissue relative to the previously acquired dataset, either or both of which are useful information for the surgeon and indicates some form of misalignment or non-concordance which should be taken into account and a correction considered.

Figure 6:
FIG. 6 shows a mock brain and the output of a navigation system showing incorrect registration of the mock brain.

In an embodiment, a surface rendering of the MR, CT, ultrasound or other medical imaging data can be generated and displayed in a way to match the viewing position and optical properties (e.g. such as zoom, field of view, etc.) of the viewing camera. As this rendering is dependent on the computed registration between the image (or MR, CT, ultrasound or other medical imaging) dataset and the physical camera position, any mis-registration will tend to be instantly visible as a misalignment in the overlay display, and can be used to dynamically validate and ensure confidence in the current registration. An example of a misalignment in the overlay display can be seen in FIG. 6.

Figure 12:
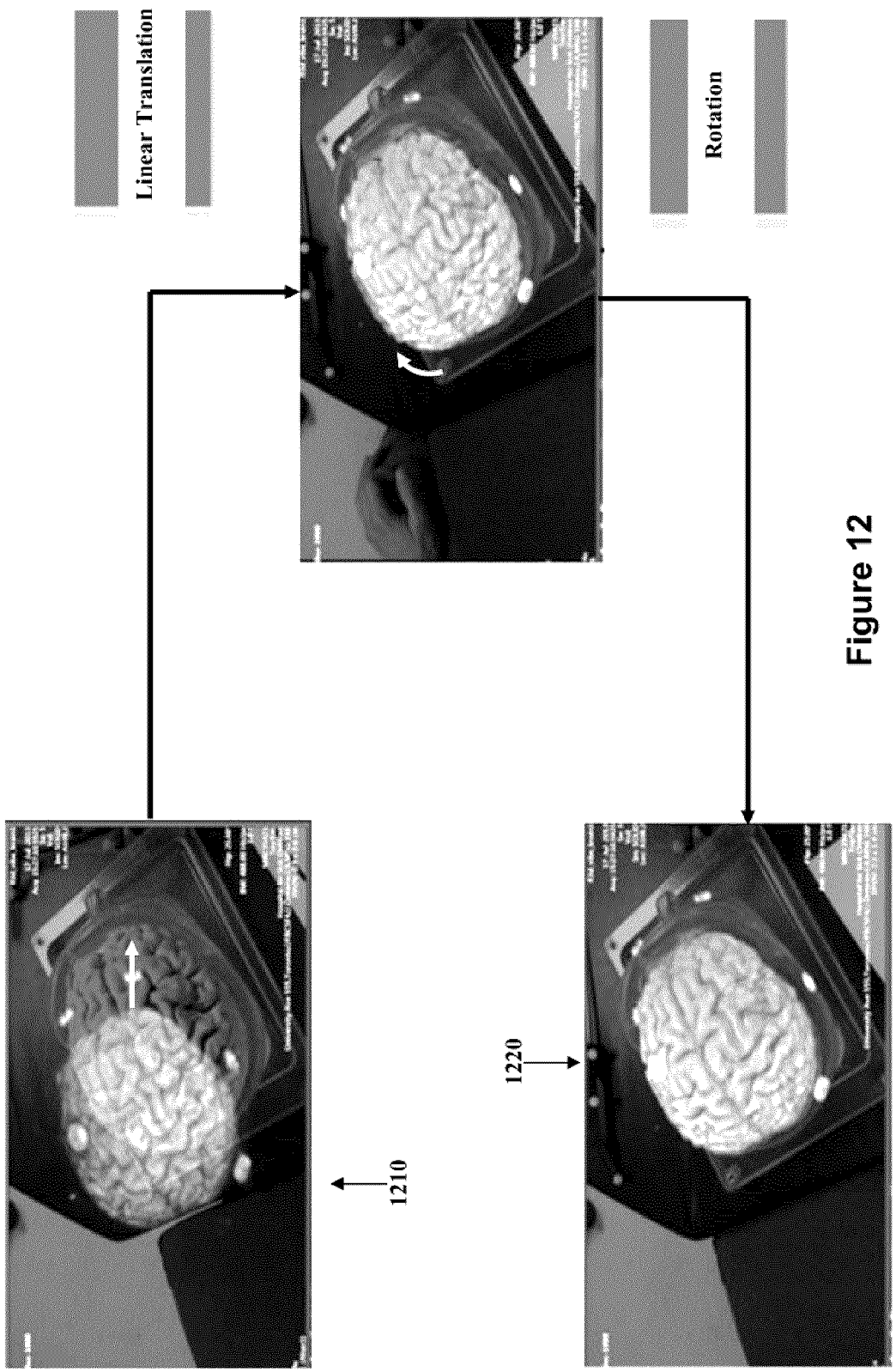
FIG. 12 shows a diagram of the navigation system showing the registration being corrected.
Figure 14:
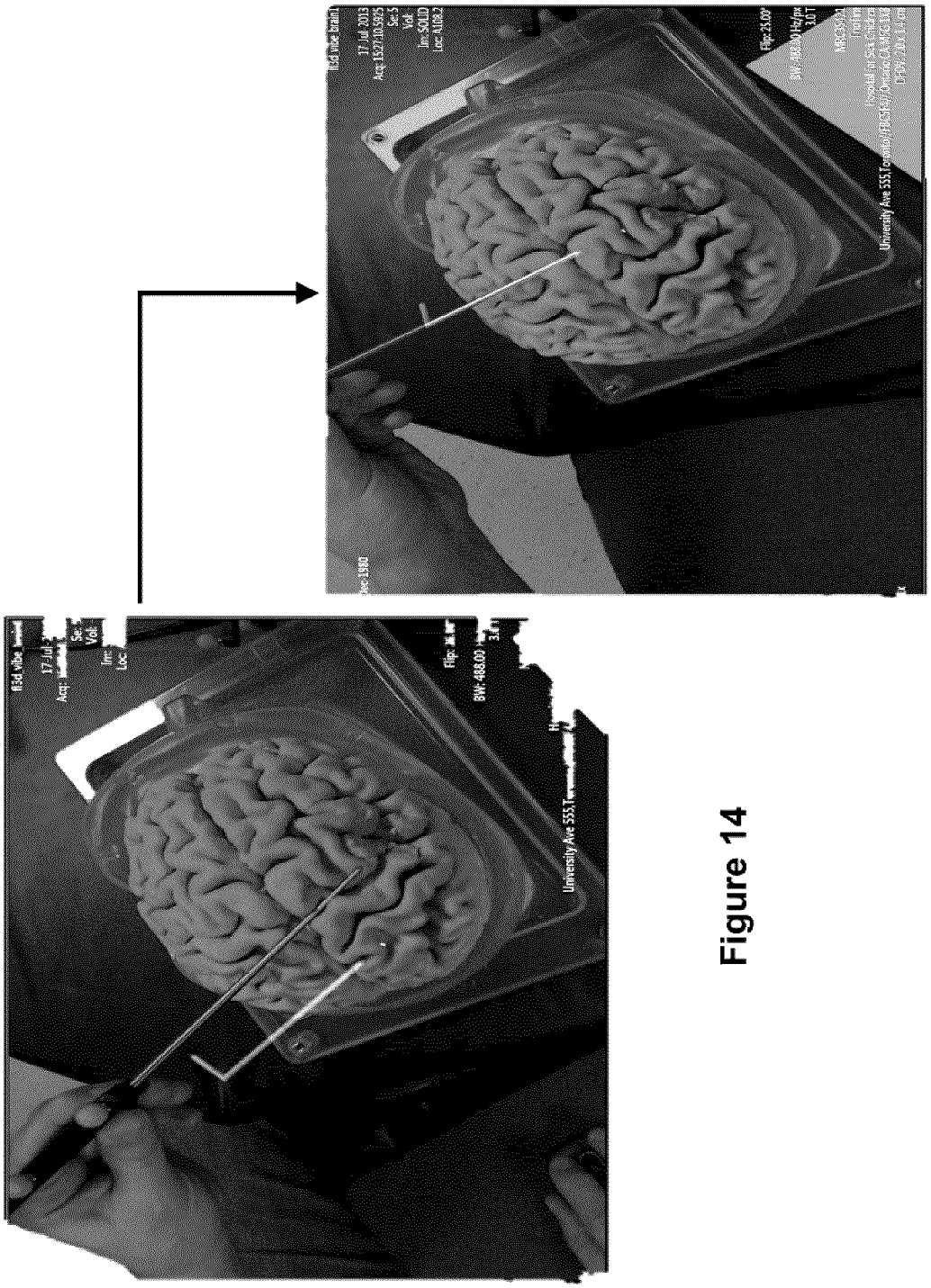
FIG. 14 shows an automatic re-registration of a virtual tracked tool with its actual counterpart.

Further, if a mis-registration is detected, a registration correction can be applied by manipulating the rendering of the MR, CT, ultrasound or other medical imaging data on the screen (for example, by rotation, translation, scaling, and any combination thereof) until it matches the overlaid video, or expressed more generally, until the virtual objects in the rendering are aligned with the real objects in the intra-operative imaging. In addition to rotation, translation, and scaling corrections, above, the rendering may also be skewed or manipulated non-linearly (such as optical flow) to generate an alignment with the real objects. Examples of linear translation, and rotation, are shown in the diagram in FIG. 12, moving from 1210 to 1220. This manipulation may be done automatically when the computer processor is programmed with instructions/algorithms to perform these manipulations and can detect when the virtual and real objects are aligned. Alternatively, the user/clinician at the surgical workstation may, through a user interface connected to the computer processer, manipulate the virtual objects manually to align them with their real counterparts in the intra-operative real time image. The applied manipulation used to achieve the coherent alignment of the virtual and real objects in the imaging data can then be used to compute an update to the registration, which may then be carried over to the overlay of the computed image of the instrument(s) from the tracking system. An example of this is shown in FIG. 14. The update to the registration of the instrument(s) is accomplished by applying the same spatial transform that was applied to the imaging data to the tracked instrument(s). This may be useful in applications where it is not desirable or possible to adjust or move a patient to achieve registration correction. In the embodiment, the correction to registration is calculated and then can be applied globally to imaging, tracking and display systems in order to validate and re-register, without any need to move or reposition a patient. A person trained in the art would appreciate that this process may be automated as well as manually applied.

Figure 20:
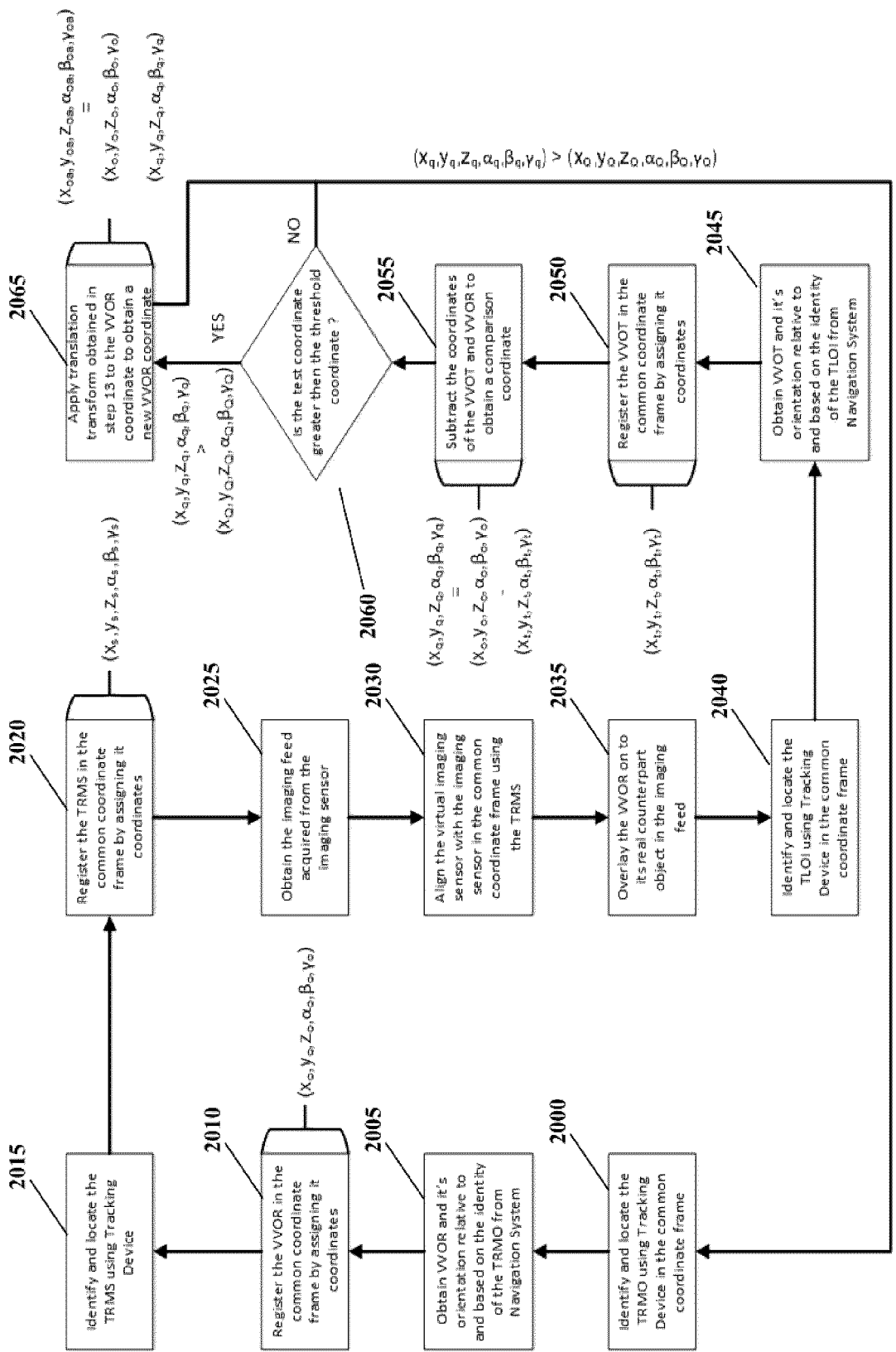
FIG. 20 shows a flow chart describing automatic detection and reregistration of a misaligned tracked object.

An example embodiment of an automatic misalignment detection and correction process is shown in FIG. 20. In the embodiment it is assumed that the virtual volumes obtainable using the optical tracking markers, and/or the template (1840), will be the same volume and that they are obtained from a database contained within the navigation system. It is also assumed that the coordinates of the volumes ($(x_o, y_o, z_o, \alpha_o, \beta_o, \gamma_o)$ and $(x_t, y_t, z_t, \alpha_t, \beta_t, \gamma_t)$ respectively) are located in the same location relative to the respective virtual volumes (i.e. the virtual optical tracking marker and template are located relative to the virtual volume in the same location as the real optical tracking markers and template are located relative to the real volume). The flow chart depicted in FIG. 20 providing an exemplary process for misalignment detection and correction is explained below in more detail.

The first step (2000) in the process is to identify and locate the Tracking Reference Marker of the Object of interest (TRMO) (for example, (1010) shown in FIG. 10 or (1830) shown in FIG. 18(*a*)) using a tracking device (such as (1140) shown in FIG. 11). The following step (2005) is to obtain the Virtual Volume of the Object of Interest (VVOR) (such as the virtual volume (310) corresponding to the object of interest (320) shown in FIG. 3) and its spatial position and pose relative to and based on the identity of the TRMO (as described above), to be overlaid on the imaging feed of the imaging sensor (for example (720) as shown in FIG. 7). Step (2010) is to register the VVOR location in the common coordinate frame by assigning it a coordinate value describing its exact location and pose in the common coordinate frame relative to the coordinates of the TRMO, as assigned below for example:

$$(x_o, y_o, z_o, \alpha_o, \beta_o, \gamma_o)$$

wherein the subscript "o" denotes the coordinates of the virtual volume of the object of interest as determined by the tracking device. The following step (2015) is to identify and locate the Tracking Reference Marker of the Imaging Sensor (TRMS) using the tracking device. Step (2020) is to register the TRMS location in the common coordinate frame by assigning it a coordinate value describing its exact location and pose in the common coordinate frame as assigned below for example:

$$(x_s, y_s, z_s, \alpha_s, \beta_s, \gamma_s)$$

wherein the subscript "s" denotes the coordinates of the imaging sensor in the common coordinate frame. The next step (2025) is to obtain the imaging feed acquired from the imaging sensor using the navigation system. The next step (2030) is to align the virtual imaging sensor with the imaging sensor in the common coordinate frame using the TRMS (i.e. so that the views of the two cameras are aligned as shown in the bottom right frame (705) of FIG. 7, as represented by the coincident alignment of both imaging sensors (710) and (720)). The following step (2035) is to overlay the VVOR onto its real counterpart object in the imaging feed via the common coordinate frame as described in this disclosure. Step (2040) is to utilize a template matching technique to determine the identity, location, and orientation of the object of interest, relative to both the coincidentally aligned virtual and actual imaging sensors ((710) and (720) respectively) by detecting the Template Located on the Object of Interest (TLOI) (for example template (1840) attached to object of interest (1820) shown in FIG. 18(*b*)). Such template matching techniques are known, examples of which are described in the paper [Monocular Model-Based 3D Tracking of Rigid Objects: A Survey; Lepetit et al. published 30 Aug. 2005; Foundations and Trends® in Computer Graphics and Vision]. It should be noted that other 3D tracking methods can be used to determine the exact location, orientation, and identity of the object of interest, also as described in the paper [Monocular Model-Based 3D Tracking of Rigid Objects: A Survey]. The next step (2045) is to obtain the virtual volume of the object of interest (VVOT) and its orientation relative to and based on the identity of the TLOI. The next step (2050) once given the object's location and orientation (its spatial position and pose) according to the TLOI relative to the imaging sensor, is to assign the VVOT of the object a coordinate value describing its exact location and orientation in the common coordinate frame relative to the coordinates of the TLOI as shown below for example:

$$(x_t, y_t, z_t, \alpha_t, \beta_t, \gamma_t)$$

wherein the subscript "t" denotes the coordinates of the virtual volume of the object of interest as determined by the imaging sensor. Step (2055) is to subtract the coordinates of the VVOT and VVOR as shown below for example:

$$(x_q, y_q, z_q, \alpha_q, \beta_q, \gamma_q) = (x_o, y_o, z_o, \alpha_o, \beta_o, \gamma_o) - (x_t, y_t, z_t, \alpha_t, \beta_t, \gamma_t)$$

wherein the subscript "q" denotes the deviation in location and orientation (spatial positioning and pose, respectively) of the overlaid and real objects in the imaging feed (for example (320) and (310) as shown in FIG. 3), and thus defines the test coordinate. This "test coordinate" is to be used as a test metric to determine the extent of misalignment. Step (2060) is to compare the obtained test coordinate in the prior step to a threshold metric to determine if the extent of misalignment of the overlaid and real objects in the imaging feed as well as the common coordinate frame exceed a threshold (for example, as shown below)

$$x_q > x_Q;$$

$$y_q > y_Q;$$

$$z_q > z_Q;$$

$$\alpha_q > \alpha_Q;$$

$$\beta_q > \beta_Q; \text{ or}$$

$$\gamma_q > \gamma_Q$$

wherein the subscript "Q" denotes the coordinates of a threshold metric used to determine if the virtual and real objects of interest are misaligned outside of a given tolerance, termed the "threshold coordinate". The next step (2065), if the test coordinate is greater than the threshold coordinate, is to convert the test coordinate obtained in step (2055) into a translation transform and apply it to the VVOT to assign it a new location relative to the TRMO in the common coordinate frame, as shown below for example:

$$(x_{oa}, y_{oa}, z_{oa}, \alpha_{oa}, \beta_{oa}, \gamma_{oa}) = (x_o, y_o, z_o, \alpha_o, \beta_o, \gamma_o) - (x_q, y_q, z_q, \alpha_q, \beta_q, \gamma_q)$$

wherein the subscript "oa" denotes the coordinates of the overlaid virtual volume (VVOR) correction. This step (2055) also entails then setting the newly obtained VVOR coordinate to complete the correction, as shown below for example:

$$(x_o, y_o, z_o, \alpha_o, \beta_o, \gamma_o) = (x_{oa}, y_{oa}, z_{oa}, \alpha_{oa}, \beta_{oa}, \gamma_{oa}).$$

step (2060), if the test coordinate is less than the threshold coordinate, or if step (2055) is completed, is to return to step (2000) and restart the loop.

In a further embodiment, the system can add registration using video overlay-match for MR, CT, ultrasound and any other imaging modality, with the addition of annotations of features on the image, (for example which may include solid outlines covering the port opening contour). These overlays can be fixed while the underlying medical image representation is manipulated (such as for a registration correction). A registration is achieved by manipulating the underlying MR to match these overlay positions, such as in the dimensions of the image data set or in three-dimensions. For example, three-dimension data points from tracked instrument(s), and patient features (such as tip of nose, corner of eyes, edge of ears, positions of bony protrusions, vessel bifurcations, etc.) may be overlaid, or the system can utilize landmarks such as a drawing of a surface of the patient or tracing structure (e.g. sulci, ears, exposed vessels) through a tool and the tracking system. An example of this may be seen depicted in the upper picture frame (810) in FIG. 8 as the inter-hemispherical fissures (820 and 830) of the rendered virtual and actual brains, respectively, are overlaid In other embodiments, overlays can be processed from the MR, CT, ultrasound or other medical images, so that they rotate with the manipulation of the medical image data, and a registration is achieved when the overlay is positioned to match the corresponding visible tissue location, for example, such as through segmentation of vessels, segmentation of tumor, skull surface tessellation, automatic detection of facial features (such as the tip or contour of nose, ears, etc.).

In one embodiment, tracking of tools may be employed to improve the rendering of the optical images. A first improvement may be obtained by masking out the upper (relative to the bottom of the access port) portion of the inserted tools/surgical instruments. Often the tools are out of focus in the optical field at the top portion of their location into the access port. Here the image often experiences glare or out of focus issues. Since the system can track the tools and register the tools with a video image, a portion of the tool may be masked out. Masking may be performed, for example, based on known geometrical models of the tools, and/or based on real-time image segmentation as described herein and in the paper noted above [Monocular Model-Based 3D Tracking of Rigid Objects: A Survey]. For example, the upper portion of the tools, or another pre-defined portion of the tools, may be masked or otherwise modified. Accordingly, image artifacts may be reduced, and the ability to utilize the entire dynamic range of the system may be improved or enabled.

Additionally, in a related embodiment, the system may be employed to replace the selected region of the tracked tool with a rendered version of the tool that follows the three-dimensional profile of the tool, optionally including rendered features such as a shadowed rendering that indicates and/or emphasizes the change in the diameter of the tool, as it is further distal in the access port. This provides an opportunity to enhance three-dimensional understanding of tool locations. The tool would then be represented with a partial real-time video view of the actual tip, and a computer rendered view of the upper portion of the tool.

By focusing the camera's gaze on the surgical area of interest, a registration update can be manipulated to ensure the best match for that region, while ignoring any non-uniform tissue deformation areas affecting areas outside the surgical field of interest. By way of example, by focusing the imaging sensor (720) on the surgical area of interest, a re-registration can be configured to ensure the best match for that particular region (as shown as (850) in the lower picture frame in FIG. 8), while ignoring any non-uniform tissue deformation areas outside such area of interest (840) as shown as (860) outside of the surgical area of interest (850) in FIG. 8. This can be particularly useful in tissue areas that have undergone small morphological changes, such as through swelling after a craniotomy opening. In these cases the misalignment may not be due to a mis-registration, but primarily due to tissue deformation.

Additionally, by matching overlay representations of tissue with an actual view of the tissue of interest, the particular tissue representation can be matched to the video image, and thus ensuring registration of the tissue of interest (850). For example, the embodiment can:
- match video of post craniotomy brain (i.e. brain exposed) with imaged sulcal map as shown in FIG. 8;
- match video position of exposed vessels with image segmentation of vessels; and/or
- match video position of lesion or tumor with image segmentation of tumor; and/or
- match video image from endoscopy up the nasal cavity with a bone rendering of bone surface on nasal cavity for endonasal alignment.

Figure 9:
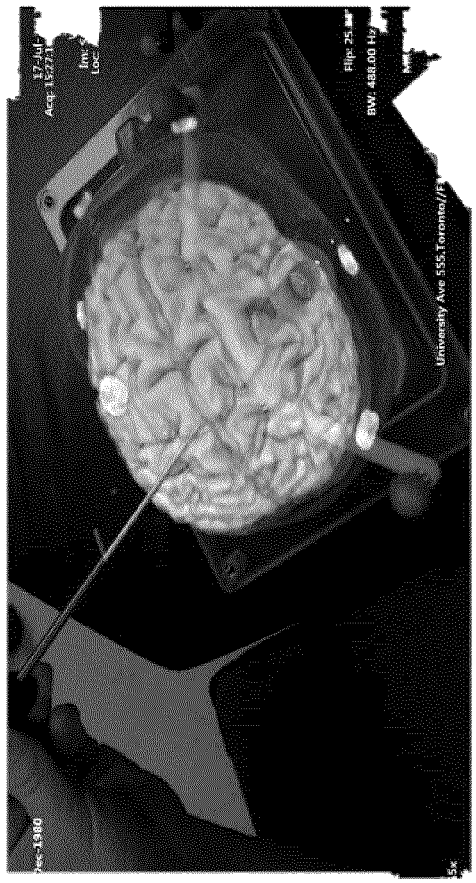
FIG. 9 shows two views of outputs of the navigation system with correct registration.
Figure 9:
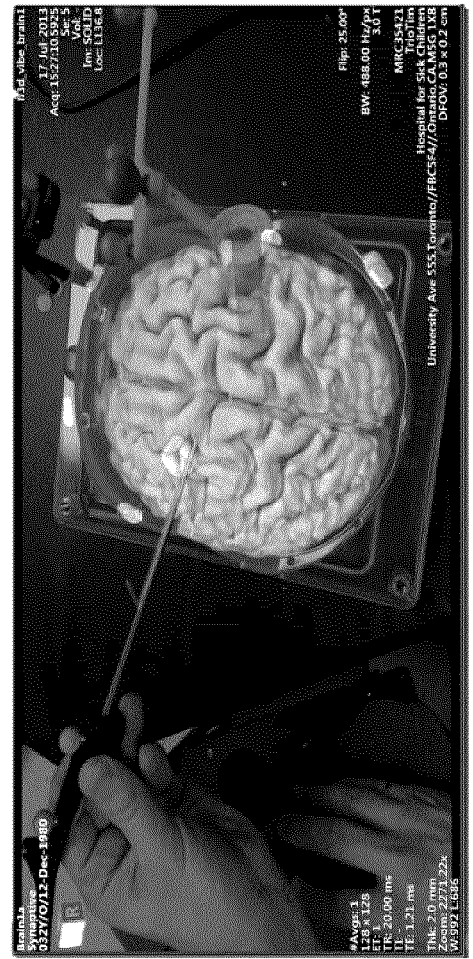

In other embodiments, multiple cameras (or a single camera moved to multiple positions) can be used and overlaid with tracked instrument(s) views, and thus allowing multiple views of the imaging data and their corresponding overlays to be presented. An example of this may be seen in the diagrams in FIG. 9. This may provide even greater confidence in a registration, or re-registration in more than one dimension/view.

In an embodiment, recovery of loss of registration may also be provided. As described above, during a navigation procedure a handheld instrument is tracked using a tracking system, and a representation of the instrument's position and orientation may be provided and displayed as an overlay on a previously acquired or current image (such as a three-dimensional scan) of a patient's anatomy obtained with an imaging device or system (such as ultrasound, CT or MRI). To achieve this, a registration is needed between the coordinate frame of a tracking system, the physical location of the patient in space, and coordinate frame of the corresponding image of the patient. In an embodiment, a registration would be needed between the physical location of the patient, as well as the corresponding image of the patient and the tracking device (1110).

In an embodiment, and as shown in FIG. 11, this registration may be obtained relative to a tracked reference marker (1010 shown in FIG. 10 and FIG. 11), which is placed in a fixed position relative to the patient anatomy of interest and thus can be used as a fixed reference for the anatomy. Generally this can be accomplished by attaching the reference marker (1010) to a patient immobilization frame (1130) (such as a clamp for skull fixation device in neurosurgery), which itself is rigidly attached to the patient. However, the reference marker (1010) may be held to the frame (1130), for example, by an arm, which may inadvertently be bumped and accidentally moved, which creates a loss of registration. Additionally, since the reference marker (1010) must be positioned so that it is visible by the navigation hardware (typically requiring line-of-sight for optical tracking, or otherwise within the observation or communication field of the tracking device (1140)) this tends to position the reference marker (1010) such that it is in the open and thus more susceptible to accidental interaction and loss of registration. In situations of lost registration, a surgical procedure tends to be stopped while a new registration is computed, although this may not always be possible if, for example, the registration fiducial points or patient skin surface are no longer accessible due to the progression of the surgical procedure, and thus creating a need for re-registration or, in some cases even disabling navigation for the remainder of the procedure.

In an embodiment, there is provided a system and method for the recovery of lost registration, while avoiding the need to perform a full re-registration. In the embodiment, provided are mechanisms for establishing backup reference positions that can be returned to in the event of a loss of registration. In the embodiment, this is provided by one or more secondary reference marker(s) being provided for navigation registration.

Figure 21:
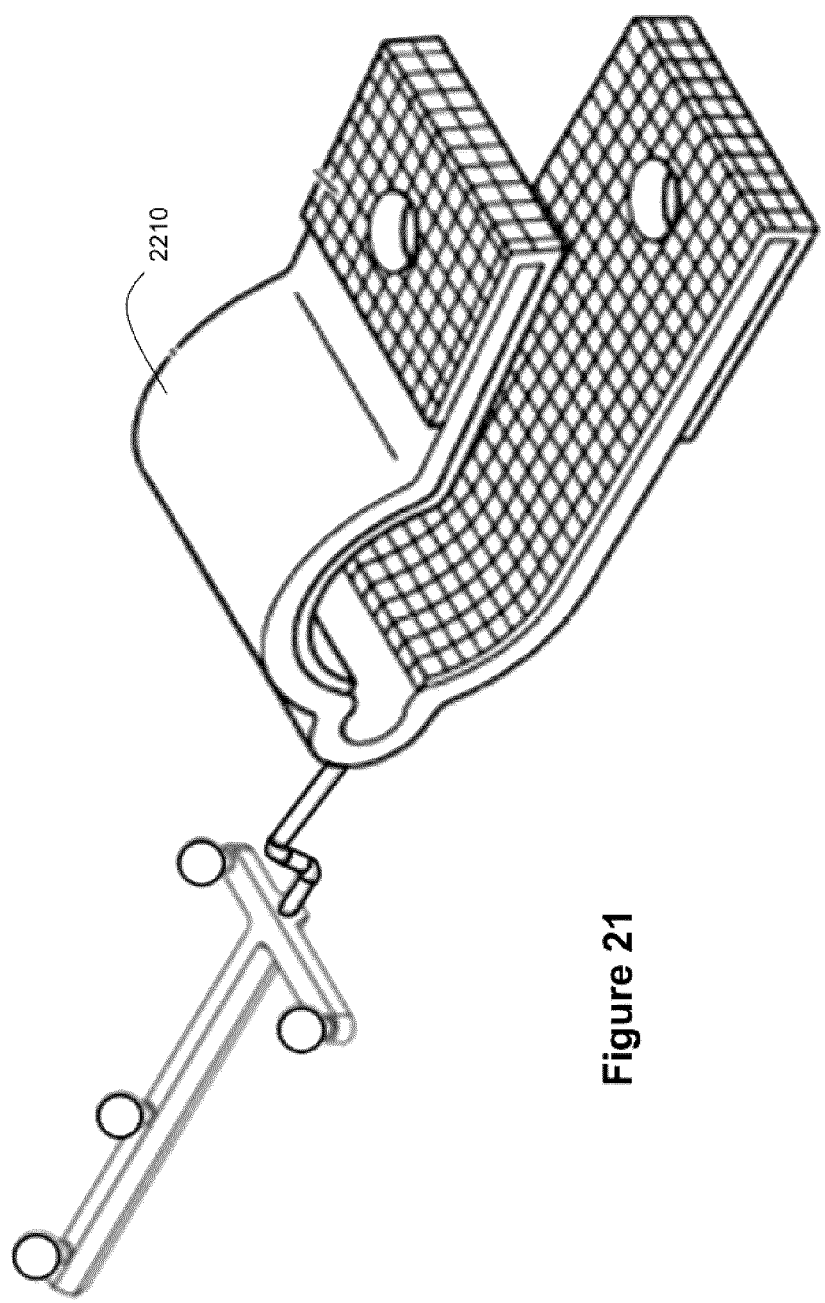
FIG. 21 shows a diagram of a removable tracking reference marker.

The one or more secondary reference marker(s) (for example as shown in FIG. 21) may be positioned during initial registration, or at any time during the procedure. The secondary reference marker(s) can optionally be removed while the standard procedure is being performed through use of the primary reference marker. A secondary reference marker that has been removed can be placed back into is original position in case a registration is lost, in order to re-establish a registration. For example, a fixture may be affixed or built into any other surface that is stationary relative to the patient during the procedure (e.g. the patient immobilization frame, the surgical table, the patient skin surface, or directly to the patient's bone) to enable a reference marker to be repeatedly attached and removed with a high degree of precision. This fixture may accommodate one or more secondary reference marker(s) and/or tool(s). These secondary reference markers and/or instruments may be repeatedly attached and removed from the fixture, as may be needed for recovery of registration. The need for repeatability of positioning of the secondary reference marker(s) may also be avoided or reduced in some embodiments if multiple fixation devices are used. For example, a surgical probe with a round shaft may be able to be positioned uniquely in all but the rotation axis about the shaft. Using multiple tracking reference tools, a best fit registration match can be determined from multiple secondary tracking reference positions so that the missing rotational information can be calculated as the registration which matches all the secondary reference positions.

A secondary reference tool(s) is attached to the fixture (or fixtures) and a registration transformation to the secondary reference tool(s) is recorded at any time after initial registration, by transforming the primary registration to the secondary marker's (or markers') position and orientation. Alternately stated, a secondary tracking reference tool(s) (shown in FIG. 21) may be attached to the fixture (or fixtures) by way of a clip (2210) for example, and a subsequent registration defined relatively to the secondary tracking reference tool(s) is recorded at any time after initial registration, by transforming the location and orientation of the initial registration's primary tracking reference to the secondary tracking reference. In various embodiments, a secondary registration can be computed at the time of the primary registration, or at any time during the procedure by using the same mechanisms (such as fiducial touch-points, surface matching, etc.) as the primary registration, thus not relying on a transformation from the primary registration but generating an independent registration to the secondary reference tool(s).

Once the registration is recorded, this secondary reference tool can optionally be removed. Since the secondary registration marker(s) does not need to be in position during the surgical procedure, the secondary reference marker(s) can be placed so that it is near the patient and occluding the surgical field. Generally, the secondary reference tool may be removed after registration, and need only be returned to the known position of a registration in order to provide recovery of lost registration of a primary (or other secondary) reference.

However, if one or more of the secondary reference(s) are maintained in position during a procedure they can also be used, which tends to improve reference position accuracy by using an average of all reference positions at all times to improve noise sensitivity in recording reference position; and/or providing a warning (such as a visual/audible) upon detection that the relative positions of the references has significantly changed. This may be used to provide an indication that one reference or both have moved and that the registration has been compromised (and so is in need for correction).

Figure 13:
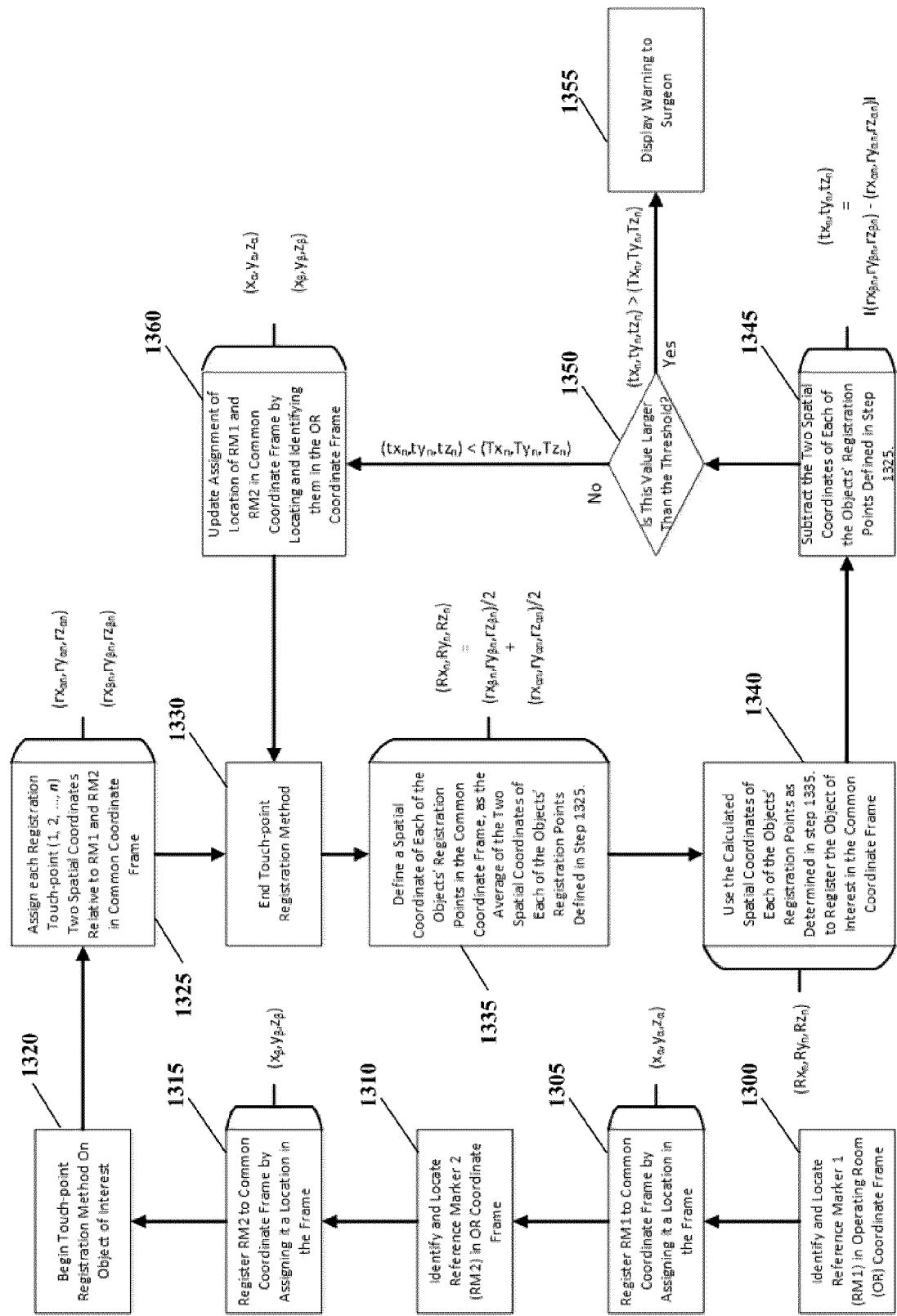
FIG. 13 shows a flow chart depicting the averaging of registration when using multiple reference markers.

FIG. 13 is a flow chart describing a non-limiting process to employ multiple reference markers during a surgery from the offset of the registration step (1515) as shown in FIG. 15. The first step (1300) in the process is to identify and locate Reference Marker 1 ("RM1") in the OR coordinate frame using the tracking device navigation system. Once located and identified the next step (1305) in the process is to incorporate RM1 into the common coordinate frame. Example coordinates being $$(x_\alpha, y_\alpha, z_\alpha)$$

Where the subscript "α" denotes that the coordinate belongs to RM1. Steps (1310) and (1315) are analogous to the two previous mentioned steps, only instead of applying the steps to RM1 the steps are applied to the second reference marker ("RM2"). Example coordinates for RM2 being $$(x_\beta, y_\beta, z_\beta)$$

Where the subscript "β" denotes that the coordinate belong to RM2. The next step (1320) is to begin registration of an object of interest with a pre-selected number of registration points in fixed and known locations with respect to it. The object of interest is to be overlaid with its virtual counterpart during the surgical procedure. Wherein the registration is completed using the touch-point method depicted in FIG. 7 and described herein. Step (1325) is to define the registration point(s) (such as, 410 in FIG. 4) (i.e. registration points 1, 2, 3, . . . , n) location(s) relative to the reference markers (such as 1010, as shown in FIG. 10) in the common coordinate frame, during the registration depicted in FIG. 7, i.e. defining registration point(s) n having coordinates relative to RM1 in the common coordinate frame as shown in the example below:

$$(rx_{\alpha n}, ry_{\alpha n}, rz_{\alpha n})=(x_\alpha+x_{r\alpha n}, y_\alpha+y_{r\alpha n}, z_\alpha+z_{r\alpha n})$$

or equivalently $$(rx_{\alpha n}, ry_{\alpha n}, rz_{\alpha n})=(Xx_\alpha, y_\alpha, z_\alpha)+(x_{r\alpha n}, y_{r\alpha n}, z_{r\alpha n}))$$

and relative to RM2 in the common coordinate frame as shown in the example below $$(rx_{\beta n}, ry_{\beta n}, rz_{\beta n})=(x_\beta+x_{r\beta n}, y_\beta+y_{r\beta n}, z_\beta+z_{r\beta n})$$

or equivalently $$(rx_{\beta n}, ry_{\beta n}, rz_{\beta n})=(x_\beta, y_\beta, z_\beta)+(x_{r\beta n}, y_{r\beta n}, z_{r\beta n})$$

Wherein the equality $$(x_\alpha+x_{r\alpha n}, y_\alpha+y_{r\alpha n}, z_\alpha+z_{r\alpha n})=(x_\beta+x_{r\beta n}, y_\beta+y_{r\beta n}, z_\beta+z_{r\beta n})$$

or equivalently $$(rx_{\alpha n}, ry_{\alpha n}, rz_{\alpha n})=(rx_{\beta n}, ry_{\beta n}, rz_{\beta n})$$

is inherently satisfied at the time of the execution of the touch-point registration method (shown in FIG. 7). And where the prefix "r" represents the coordinates of the registration points and the subscripts "αn", and "βn", denote the $n^{th}$ registration points' coordinate relative to the common coordinate frame calculated using their positions relative to RM1 and RM2 respectively and "rαn", and "rβn" denote the $n^{th}$ registration points' coordinates relative to RM1 and RM2 respectively. It should be noted that the coordinate points $(x_\alpha, y_\alpha, z_\alpha)$ and $(x_\beta, y_\beta, z_\beta)$ are dynamic given that they are the positional coordinate of RM1 and RM2 respectively in real-time (i.e. they are periodically updated by the tracking device with respect to their current locations in the common coordinate frame). On the other hand the coordinate point locations $(x_{r\beta n}, y_{r\beta n}, z_{r\beta n})$ and $(x_{r\beta n}, y_{r\beta n}, z_{r\beta n})$ are defined relative to the position of the Reference Markers (RM1 and RM2 respectively) and are constant and unchanging throughout the surgical procedure until such a time that a touch point registration process is executed again. After the registration is completed, step (1330), step (1335) in the process is to define the location of the registration points (1 to n) as:

$$(Rx_n, Ry_n, Rz_n)=[(x_\alpha+x_{r\alpha n}, y_\alpha+y_{r\alpha n}, z_\alpha+z_{r\alpha n})+(x_\beta+x_{r\beta n}, y_\beta+y_{r\beta n}, z_\beta+z_{r\beta n})]/2$$

or equivalently $$(Rx_n, Ry_n, Rz_n)=(([(x_\alpha+x_{r\alpha n})+(x_\beta+x_{r\beta n})]/2),$$

$$([(y_\alpha+y_{r\alpha n})+(y_\beta+y_{r\beta n})]/2),([(z_\alpha+z_{r\alpha n})+(z_\beta+z_{r\beta n})]/2))$$

or equivalently $$(Rx_n, Ry_n, Rz_n)=[(rx_{\beta n}, ry_{\beta n}, rz_{\beta n})+(rx_{\alpha n}, ry_{\alpha n}, rz_{\alpha n})]/2$$

Where the prefix R denotes the n registration point(s) average coordinates based on their relative location of two reference markers (RM1 and RM2). Step (1340) is to use the calculated point(s) $(Rx_n, Ry_n, Rz_n)$ (1 to n) to register the real object in the common coordinate frame so it can be overlaid with its virtual counterpart. It should be noted that if the coordinates of RM1 and RM2 are constant throughout the procedure the equality $$(x_\alpha + x_{r\alpha n}, y_\alpha + y_{r\alpha n}, z_\alpha + z_{r\alpha n}) = (x_\beta + x_{r\beta n}, y_\beta + y_{r\beta n}, z_\beta + z_{r\beta n})$$

will be satisfied, resulting in the following $$(Rx_n, Ry_n, Rz_n) = (rx_{\beta n}, ry_{\beta n}, rz_{\beta n}) = (rx_{\alpha n}, ry_{\alpha n}, rz_{\alpha n})$$

This implies the relative position of the registration points (1 to n) will remain in an unchanged location (i.e. have constant coordinates) in the common coordinate frame equivalent to the initial touch-point registration coordinates. However if the points RM1 and/or RM2 change then the equality is broken and an averaged position located at the midpoints of the registration point sets relative to both RM1 (i.e. $(rx_{\alpha n}, ry_{\alpha n}, rz_{\alpha n})$) and RM2 (i.e. $(rx_{\beta n}, ry_{\beta n}, rz_{\beta n})$) are calculated and used to determine the location of the virtual object overlay in the common coordinate frame.

The next three (3) steps in the process involve identifying any potential shifts of the reference marker locations to the point where the registration becomes inaccurate (as defined by a threshold value). Step (1345) indicates that the instantaneous (last updated) registration points relative to RM1 and RM2 must be subtracted and their absolute value calculated and defined as the total deviation and denoted with a prefix "t" as in the following example $$(tx_n, ty_n, tz_n) = |(rx_{\beta n}, ry_{\beta n}, rz_{\beta n}) - (rx_{\alpha n}, ry_{\alpha n}, rz_{\alpha n})|$$

Once calculated step (1350) indicates the total deviation of the instantaneous (last updated) registration points relative to RM1 and RM2 will be compared to a threshold value defined by the user as shown in the following example If $$tx_n < Tx_n$$

or $$ty_n < Ty_n,$$

or $$tz_n < Tz_n$$

where the prefix "T" indicates the coordinate threshold values, then the process continues a loop by initiating step (1360) which is to update of the assigned location of RM1 and RM2

(i.e. $(x_\alpha, y_\alpha, z_\alpha)$ and $(x_\beta, y_\beta, z_\beta)$ respectively)

in the common coordinate frame returning followed by returning to step (1335). However if $(tx_n, ty_n, tz_n) > (Tx_n, Ty_n, Tz_n)$, then the process moves to step (1355) and indicates to the surgeon that the registration of the object is inaccurate.

In an embodiment having multiple reference tools, it is possible to infer which reference tool has moved, by determining the one that has shifted position most significantly relative to a camera, and so this reference tool can automatically be dropped from calculation and the procedure can continue without interruption. In the embodiment, once a moved reference position has stabilized, a new position for the reference can be recorded and it can automatically be returned to function as a fixed reference in its new position, again, without interruption.

In use, if at any time during a procedure, a primary reference marker (1010) or instrument is moved and registration is lost (or, in effect considered no longer reliable), one or more secondary reference marker(s) or instruments(s) (that were previously registered can be affixed to the fixture and the secondary registration can be re-established using the secondary marker(s) or instruments(s). The procedure can continue using the secondary reference marker, or the secondary reference marker(s) or instruments(s) can be used as a fixed point to compute an updated registration to the (now) moved position of the primary reference, so that the procedure can continue using the updated primary reference registration. At that point the secondary reference marker(s) can optionally be removed from the fixation device, since registration using the primary reference marker (1010) would then be updated to reflect the moved position of the primary reference marker or instruments(s).

In an embodiment, a secondary reference marker or tool can be a separate tracking tool, or it can be a sterile, tracked surgical hand-piece or pointer, each of which would have been registered to a fixation fixture, which can be (re) attached temporarily to the fixation fixtures to re-establish a lost registration.

In some embodiments, multiple fixation fixtures can be provided and placed at any convenient position, each capable of holding a secondary reference marker(s) and/or having a handpiece or pointer initialized locations. In the embodiment, at any time during the procedure, any one of these fixtures can be used to re-establish or refine a registration by re-attaching the marker(s). In an example, secondary markers can be inclusive of both the tracking reference marker (1010) and the tracking sensor (1140).

In an embodiment, the fixation fixture may be a disposable clip that adheres, straps or screws into place. As noted above, FIG. 10 shows a diagram of a tracking reference to which passive tracking markers (1020) are affixed in a known and fixed location with respect to the anatomical part undergoing the medical procedure, in this case a patient's brain.

In an embodiment, a reference position may be provided, which allows a tracking camera to be moved dynamically during a procedure to ensure a good line-of-sight with the tracked instruments. Another method of recovering registration is based on the ability to temporarily lock the tracking camera in a fixed position relative to the patient. An example of an embodiment is shown in FIG. 11 in the right hand frame (1105). The system (and associated control software) can be placed into a "camera fixed" mode, at which time the tracking camera is not allowed to move relative to the patient. In the "camera fixed" mode, the registration is established relative to this fixed camera, regardless of the position of the reference marker, and thus in essence making the camera position itself the fixed reference.

In this embodiment, if the camera position needs adjustment, then the system may be placed into a "reference fixed" position, which establishes a registration relative to the position of the reference, and thereafter allows the camera to be moved to a new position without affecting the registration. The embodiment can also subsequently return to the "camera fixed" mode to again provide independence from the registration marker. An example embodiment of the system in "reference fixed" mode is shown in FIG. 11. In the left hand frame (1100) the camera (1140) is moved (1150) to a new position while the patient is registered to the reference frame (1120) of the reference marker (1010). This embodiment can be extended to allow the system to enter a "tool X fixed" mode (where X represents any one of the available tracked tools), where any tool can be asserted to be remaining fixed in relative to the patient, and the registration can transfer to that tool X position. Afterward, the procedure can continue with that tool as a reference, or the system can be subsequently returned to a "reference fixed" mode once the primary reference is not moving relative to the patient, and the procedure continues with the registration transferred to the original primary reference tool.

However, in typical use during a procedure, after initial registration typically it will be advantageous that neither the tracking system sensor nor the reference marker be moved relative to the patient. A registration that averages a camera-fixed and reference-fixed computed transformation can be used to provide a more accurate registration in some embodiments. An algorithm for averaging a registration based upon two reference markers is depicted in FIG. 13.

The system can also permit for "camera fixed" and "reference fixed" modes (or any combination of "tool X fixed" modes) to be enabled at the same time. In an embodiment, the restriction would be that a system state of "camera movable" and "reference movable" cannot be enabled together, or stated more generally, there must always be at least one tool remaining in "fixed mode" to act as a fixed patient reference. In an embodiment, the system can be configured to respond to an automatic signal sent when the camera mount is unlocked for movement, thus switching out of camera locked mode automatically when the camera is being moved and shifting back when the camera position is again locked.

The tracking of movement of a reference marker or tool can be monitored during a procedure, and a warning can be displayed or sounded if the reference has been moved relative to any other fixed reference.

In another embodiment, the use of secondary reference marker(s) and a tracking camera (1140) can be combined to provide a registration validation, where no fixed reference marker (1010) is required. In the embodiment, a tracking tool may be affixed to a fixation fixture and the registration is established relative to the tracking tool prior to moving the tracking sensor. After the tracking sensor is positioned and the registration is returned to be relative to the tracking sensor position, the reference tracking tool can then be removed. In the embodiment, the camera may be considered as a virtual secondary reference tool at the origin of the camera reference frame, which camera tends to serve the same function as the secondary reference marker or tool as described above in other embodiments At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, C#, SQL or any other suitable programming language and may comprise modules or classes, as is known to those skilled in object oriented programming. At least some of the elements of the system 10 that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed is:

1. A computer-implemented method of detecting registration error during a medical procedure by way of a surgical navigation system comprising a tracking system, the tracking system having an imaging system, the method comprising:

acquiring, in real-time, using an actual camera having a virtual camera aligned therewith, intraoperative imaging of a surgical field containing one or more real objects, the one or more real objects being previously registered with one or more corresponding virtual objects, the actual camera and the one or more real objects being previously registered, via the tracking system, to a common coordinate frame relative to a tracked reference marker, and the tracked reference marker disposed in a fixed position relative to a patient anatomy;

displaying the intraoperative imaging on a display of a display system;

acquiring, using the virtual camera, virtual imaging containing the one or more virtual objects in the common coordinate frame;

overlaying, in real-time during the procedure, the virtual imaging onto the intraoperative imaging on the display;

detecting any misalignment between any one of the one or more previously registered real objects contained in the intraoperative imaging and the corresponding virtual object contained in the virtual imaging and overlaid on the intraoperative imaging, wherein a presence of misalignment is indicative of registration error between the virtual object and the corresponding real object, and wherein a coordinate frame of the surgical navigation system is spatially registered with a coordinate frame of patient imaging data through respective alignment of corresponding pairs of virtual points and actual points;

automatically correcting the misalignment based on a difference between local tissue characteristics and virtual instrument representations at a location being focused and a live video stream of the surgical field, thereby providing immediate local correction of registration, automatically correcting comprising nonlinearly manipulating a rendering of the patient imaging and the virtual imaging to align with the intraoperative imaging, nonlinearly manipulating comprising using optical flow to generate an alignment with real objects; and globally applying the correction of registration to the imaging system, the tracking system, and the display system, thereby providing dynamic validation and re-registration, and thereby eliminating need to reposition a patient.

2. The method according to claim 1, wherein, if a misalignment is detected in the detecting step, further comprising:

applying at least one of translating, rotating, skewing, and scaling of the virtual object in the common coordinate frame to align the virtual object with the corresponding real object in the common coordinate frame for re-registering the virtual object; and assigning the reregistered virtual object as the previously registered virtual object in the common coordinate frame.

3. The method according to claim 2,
wherein at least one of the one or more real objects comprises an anatomical part undergoing the medical procedure, and
wherein at least one of the one or more pre-registered virtual objects in the virtual image comprises a preoperative image of the anatomical part.

4. The method according to claim 2,
wherein at least one of the one or more real objects comprises a medical instrument, and
wherein at least one of the one or more pre-registered virtual objects in the virtual image comprises a virtual image of at least one medical instruments.

5. The method according to claim 1,
wherein at least one of the one or more real objects comprises an anatomical part undergoing the medical procedure,
wherein at least one of the one or more pre-registered virtual objects in the virtual image comprises a preoperative image of the anatomical part,
wherein at least one of the one or more real objects comprises a medical instrument, and
wherein at least one of the one or more preregistered virtual objects in the virtual image comprises a virtual image of at least one medical instruments.

6. The method according to claim 3, wherein the anatomical part comprises a brain of a human patient.

7. The method according to claim 6,
wherein said surgical field comprises landmarks, and
wherein the landmarks comprises at least one of morphological features intrinsically associated with the brain, a head of the human patient, and a face of the human patient.

8. The method according to claim 6,
wherein said surgical field comprises landmarks, and
wherein the landmarks comprise a plurality of fiducials placed in fixed and known positions with respect to the brain of the human patient.

9. The method according to claim 8, wherein the plurality of fiducials comprises at least one of a plurality of active fiducials and a plurality of passive fiducials.

10. The method according to claim 6,
wherein said surgical field comprises a plurality of landmarks,
wherein the plurality of landmarks comprises at least one of a plurality of morphological features intrinsically associated with the anatomical part and a plurality of fiducials placed in preselected positions with respect to said anatomical part, and
wherein said plurality of fiducials are disposed in a field of view of a tracking device.

11. The method according to claim 6,
wherein at least one of the one or more real objects comprises a surgical port, and
wherein at least one of the one or more preregistered virtual objects in the virtual image comprises a virtual image of the surgical port.

12. The method according to claim 10, using a computer processor programmed with instructions, further comprising:

receiving input the input specifying at least one of translating, rotating, skewing, and scaling the virtual object in the coordinate frame of said surgical navigation system to align the virtual object with its corresponding real object in the coordinate frame of said surgical navigation system;

re-registering the virtual object, thereby providing a re-registered virtual object;

storing the re-registered virtual object in the coordinate frame of said surgical navigation system; and assigning the re-registered virtual object as a previously registered virtual object.

13. The method according to claim 10,
wherein, in the event of a misalignment between at least one of said one or more virtual objects and its corresponding real object at a pre-selected time, performing at least one of translating, rotating, skewing, and scaling of the virtual object in the coordinate frame of said surgical navigation system to align the virtual object with the corresponding real object in the coordinate frame of said surgical navigation system and re-registering the virtual object, and
wherein said computer processor is programmed with instructions to store the re-registered virtual object in the coordinate frame of said surgical navigation system and assigning the re-registered virtual object as the previously registered virtual object.

14. The method according to claim 5, wherein the anatomical part comprises a brain of a human patient.

15. The method according to claim 1, wherein acquiring the virtual image comprises using one of CT imaging, MRI imaging, X-Ray imaging, PET imaging, or ultrasound imaging.

16. The method according to claim 15, wherein the anatomical part comprises a brain of a human patient.

* * * * *